US009249391B2

(12) United States Patent
Huang et al.

(10) Patent No.: US 9,249,391 B2
(45) Date of Patent: Feb. 2, 2016

(54) METHODS OF GENERATING NEURAL STEM CELLS

(71) Applicant: The J. David Gladstone Institutes, San Francisco, CA (US)

(72) Inventors: Yadong Huang, San Francisco, CA (US); Karen Ring, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 14/335,246

(22) Filed: Jul. 18, 2014

(65) Prior Publication Data
US 2015/0017139 A1    Jan. 15, 2015

Related U.S. Application Data

(60) Division of application No. 13/467,475, filed on May 9, 2012, now Pat. No. 8,815,589, which is a continuation-in-part of application No. PCT/US2010/055836, filed on Nov. 8, 2010.

(60) Provisional application No. 61/259,885, filed on Nov. 10, 2009.

(51) Int. Cl.
*C12N 5/00* (2006.01)
*C12N 5/02* (2006.01)
*C12N 5/0797* (2010.01)

(52) U.S. Cl.
CPC .......... *C12N 5/0623* (2013.01); *C12N 2501/11* (2013.01); *C12N 2501/115* (2013.01); *C12N 2501/602* (2013.01); *C12N 2501/91* (2013.01); *C12N 2502/99* (2013.01); *C12N 2506/1307* (2013.01); *C12N 2510/00* (2013.01)

(58) Field of Classification Search
CPC .................................................... C12N 5/0623
See application file for complete search history.

(56) References Cited

U.S. PATENT DOCUMENTS

| | | | |
|---|---|---|---|
| 7,314,721 B2 | 1/2008 | Gure et al. | |
| 8,211,697 B2 * | 7/2012 | Sakurada et al. | 435/377 |
| 8,815,589 B2 | 8/2014 | Huang et al. | |
| 2005/0032207 A1 | 2/2005 | Wobus et al. | |
| 2008/0260829 A1 | 10/2008 | Hidaka et al. | |
| 2009/0035284 A1 | 2/2009 | Daadi et al. | |
| 2009/0047263 A1 | 2/2009 | Yamanaka et al. | |
| 2009/0117639 A1 | 5/2009 | Carpenter | |
| 2009/0191159 A1 | 7/2009 | Sakurada et al. | |

FOREIGN PATENT DOCUMENTS

| | | |
|---|---|---|
| WO | WO2009-067563 | 5/2009 |
| WO | WO2009-079007 | 6/2009 |

OTHER PUBLICATIONS

Kim, et al., "Direct Reprogramming of Human Neural Stem Cells by OCT4", Nature, 2009, vol. 461, 6 pages.
Merkl, et al., "Efficient Generation of Rat Induced Pluripotent Stem Cells Using a Non-Viral Inducible Vector", PLos One, 2013, vol. 8, Issue 1, 13 pages.
Mohamad, et al., "Vector-Free and Transgene-Free Human iPS Cells Differentiate into Functional Neurons and Enhance Functional Recovery after Ischemic Stroke in Mice", PLos One. 2013.vol. 8. Issue 5. 12 pages.
Motoyama, et al., "In vitro Reprogramming of Adult Hepatocytes into Insulin-Producing Cells Without Viral Vectors", Biochemical and Biophysical Research Communications, 2009. vol. 385. pp. 123-128.
Peng, et al., "Delivery of Oct4 and SirT1 with Cationic Polyurethanes-Short Branched PEI to Aged Retinal Pigment Epithelium", Biomaterials, 2011, vol. 32, pp. 9077-9088.
Schott, et al., "Viral and Non-Viral Approaches for Transient Delivery of mRNA and Proteins", Current Gene Therapy, 2011, vol. 11, pp. 382-398.
Sun, et al., "Feeder-free Derivation of Induced Pluripotent Stem Cells from Adult Human Adipose Stem Cells", PNAS, 2009, vol. 106, No. 37, 6 pages.
Takahashi, et al., "Induction of Pluripotent Stem Cells from Mouse Embryonic and Adult Fibroblast Cultures by Defined Factors", Cell, 2006, vol. 126, pp. 663-676.
Wernig, et al., "A Drug-Induced Transgenic System for Direct Reprogramming of Multiple Somatic Cell Types", Nat Biotechnol., 2008, vol. 26, No. 8, 20 pages.
Yu, et al., "Human Induced Pluripotent Stem Cells Free of Vector and Transgene Sequences", Science, 2009, vol. 324, No. 5928, 9 pages.

\* cited by examiner

*Primary Examiner* — Valarie Bertoglio
(74) *Attorney, Agent, or Firm* — Michael B. Rubin; Bozicevic, Field & Francis LLP

(57) ABSTRACT

The present disclosure provides methods of generating neural stem cells from differentiated somatic cells. The present disclosure also provides induced neural stem cells generated using a subject method, as well as differentiated cells generated from a subject induced neural stem cell. A subject neural stem cell, as well as differentiated cells derived from a subject neural stem cell, is useful in various applications, which are also provided in the present disclosure.

10 Claims, 8 Drawing Sheets

*Homo sapiens* Sox2

```
  1 mynmmetelk ppgpqqtsgg gggnstaaaa ggnqknspdr vkrpmnafmv wsrggrrkma
 61 qenpkmhnse iskrlgaewk lisetekrpf ideakrlral hmkehpdyky rprrktktlm
121 kkdkytlpgg llapggnsma sgvgvgaglg agvngrmdsy ahmngwsngs ysmmqdqlgy
181 pqhpglnahg aaqmqpmhry dvsalqynsm tssqtymngs ptysmsysqq gtpgmaigsm
241 gsvvkseass sppvvtsssh srapcqagdl rdmismylpg aevpepaaps rlhmsqhyqs
301 gpvpgtaing tiplshm
```

SEQ ID NO:1

FIG. 8A

*Homo sapiens* Sox2

```
  1 atgtacaaca tgatggagac ggagctgaag ccgcccgggc cgcagcaaac ttcgggggc
 61 ggcgggggca actccacccg cgcggcggcc ggcgggcaaa agaaaaacag cccggaccgc
121 gtcaagcggc ccatgaatgc cttcatggtg tggtcccgcg ggcagcggcg caagatggcc
181 caggagaacc ccaagatgca caactcggag atcagcaagc gcctgggcgc cgagtggaaa
241 ctttgtcgg agacggagaa gcggccgttc attaaaatac cggacccgga ctaagcggct
301 cacatgaagg agcacccgga ttataaatac cggccccggg ggaaaaccaa gacgctcatg
361 aagaaggata gttacacgct gcccggcggc ccggcggcaa tagcaggcg
421 agcggggtcg gggtgggcgc acggctggag ggggcgtga accagcgcat ggacagttac
481 gcgcacatga acgggtggag caacggcagc tacagcatga tgcaggacca gctgggctac
541 ccgcagcacc cggggctcaa tgcgcacggc gcagcgcaga tgcagcccat gcaccgctac
601 gacgtgagcg cctgcagta caactccatg accagctcgc agacctacat gaacggctcg
661 ccccactaca gcatgtccta ctcgcagcag ggcaccccctg gcatggctct tggctccatg
721 ggttcggtgg tcaagtccga ggccagctcc agccccctg tggttaccc ttcctcccac
781 tccccagccg cctgccagc cggggacctc cgggacatga tcagcatgta tctgcccggg
841 gccgaggtgc cggaaccgc cgcgccagc cggacttcaca tgtcccagca ctaccagagc
901 ggcccggtgc ccggcacggc cattaacggc acactgcccc tctcacacat gtga
```

SEQ ID NO:2

FIG. 8B

SEQUENCE LISTING

```
<160> NUMBER OF SEQ ID NOS: 11

<210> SEQ ID NO 1
<211> LENGTH: 317
<212> TYPE: PRT
<213> ORGANISM: Homo sapiens

<400> SEQUENCE: 1

Met Tyr Asn Met Met Glu Thr Glu Leu Lys Pro Pro Gly Pro Gln Gln
 1               5                  10                  15

Thr Ser Gly Gly Gly Gly Asn Ser Thr Ala Ala Ala Ala Gly Gly
             20                  25                  30

Asn Gln Lys Asn Ser Pro Asp Arg Val Lys Arg Pro Met Asn Ala Phe
         35                  40                  45

Met Val Trp Ser Arg Gly Gln Arg Arg Lys Met Ala Gln Glu Asn Pro
     50                  55                  60

Lys Met His Asn Ser Glu Ile Ser Lys Arg Leu Gly Ala Glu Trp Lys
 65                  70                  75                  80

Leu Leu Ser Glu Thr Glu Lys Arg Pro Phe Ile Asp Glu Ala Lys Arg
                 85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
        130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315
```

<210> SEQ ID NO 2
<211> LENGTH: 954
<212> TYPE: DNA
<213> ORGANISM: Homo sapiens

<400> SEQUENCE: 2

```
atgtacaaca tgatggagac ggagctgaag ccgccgggcc cgcagcaaac ttcgggggc      60
ggcggcggca actccaccgc ggcggcggcc ggcggcaacc agaaaaacag cccggaccgc    120
gtcaagcggc ccatgaatgc cttcatggtg tggtcccgcg ggcagcggcg caagatggcc    180
caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcacccgga ttataaatac cggccccggc ggaaaaccaa gacgctcatg    360
aagaaggata gtacacgct gcccggcggg ctgctggccc ccggcggcaa tagcatggcg    420
agcggggtcg gggtgggcgc cggcctgggc gcgggcgtga accagcgcat ggacagttac    480
gcgcacatga acggctggag caacggcagc tacagcatga tgcaggacca gctgggctac    540
ccgcagcacc cgggcctcaa tgcgcacggc gcagcgcaga tgcagcccat gcaccgctac    600
gacgtgagcg ccctgcagta caactccatg accagctcgc agacctacat gaacggctcg    660
cccacctaca gcatgtccta ctcgcagcag ggcacccctg gcatggctct ggctccatg     720
ggttcggtgg tcaagtccga ggccagctcc agccccctg tggttacctc ttcctcccac     780
tccagggcgc cctgccaggc cggggacctc cgggacatga tcagcatgta tctccccggc    840
gccgaggtgc cggaacccgc cgccccagc agacttcaca tgtcccagca ctaccagagc    900
ggcccggtgc ccggcacggc cattaacggc acactgcccc tctcacacat gtga          954
```

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Tyr Gly Arg Lys Lys Arg Arg Gln Arg Arg Arg
 1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Arg Arg Gln Arg Arg Thr Ser Lys Leu Met Lys Arg
 1               5                   10

<210> SEQ ID NO 5
<211> LENGTH: 27
<212> TYPE: PRT
<213> ORGANISM: Artificial Sequence
<220> FEATURE:
<223> OTHER INFORMATION: Synthetic peptide

```
<400> SEQUENCE: 5

Gly Trp Thr Leu Asn Ser Ala Gly Tyr Leu Leu Gly Lys Ile Asn Leu
  1               5                  10                  15

Lys Ala Leu Ala Ala Leu Ala Lys Lys Ile Leu
             20                  25

<210> SEQ ID NO 6
<211> LENGTH: 33
<212> TYPE: PRT
<213> ORGANISM: Artificial Sequence
<220> FEATURE:
<223> OTHER INFORMATION: Synthetic peptide

<400> SEQUENCE: 6

Lys Ala Leu Ala Trp Glu Ala Lys Leu Ala Lys Ala Leu Ala Lys Ala
  1               5                  10                  15

Leu Ala Lys His Leu Ala Lys Ala Leu Ala Lys Ala Leu Lys Cys Glu
             20                  25                  30

Ala

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Arg Gln Ile Lys Ile Trp Phe Gln Asn Arg Arg Met Lys Trp Lys Lys
  1               5                  10                  15

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Lys Lys Arg Arg Gln Arg Arg Arg
  1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Tyr Ala Arg Ala Ala Ala Arg Gln Ala Arg Ala
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Thr His Arg Leu Pro Arg Arg Arg Arg Arg
  1               5                  10
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Gly Gly Arg Arg Ala Arg Arg Arg Arg Arg Arg
1               5                   10
```

METHODS OF GENERATING NEURAL STEM CELLS

CROSS-REFERENCE

This application is a divisional application of U.S. patent application Ser. No. 13/467,475, filed May 9, 2012, now U.S. Pat. No. 8,815,589, which is a continuation-in-part application of PCT/US2010/055836, having an international filing date of Nov. 8, 2010, which applications are incorporated herein by reference in their entirety. This application claims the benefit of U.S. Provisional Patent Application No. 61/259,885, filed Nov. 10, 2009, which application is incorporated herein by reference in its entirety.

BACKGROUND

The use of pluripotent and multipotent stem cells in the field of regenerative medicine has garnered much interest in recent years. Various methods have been employed to reprogram somatic cells to become pluripotent stem cells. Nevertheless, there remains a need in the art for methods of generating multipotent cells, such as neural stem cells (NSCs), from somatic cells.

LITERATURE

U.S. Patent Publication Nos. 2009/0047263, 2009/0035284, 2009/0191159; 2009/0117639; Takahashi and Yamanaka (2006) *Cell* 126:663; Kim et al. (Aug. 28, 2009) *Nature* 461:649 (PMID: 19718018).

SUMMARY OF THE INVENTION

The present disclosure provides methods of generating an induced neural stem cell (iNSC) from a differentiated somatic cell. The present disclosure also provides iNSCs generated using a subject method, as well as differentiated cells generated from a subject iNSC. A subject iNSC, as well as differentiated cells derived from a subject iNSC, is useful in various applications, which are also provided in the present disclosure.

BRIEF DESCRIPTION OF THE DRAWINGS

FIGS. 8A and 8B provide an amino acid sequence of a Sox2 polypeptide (FIG. 8A); and a nucleotide sequence (FIG. 8B) encoding a Sox2 polypeptide.

DEFINITIONS

Figure 1:
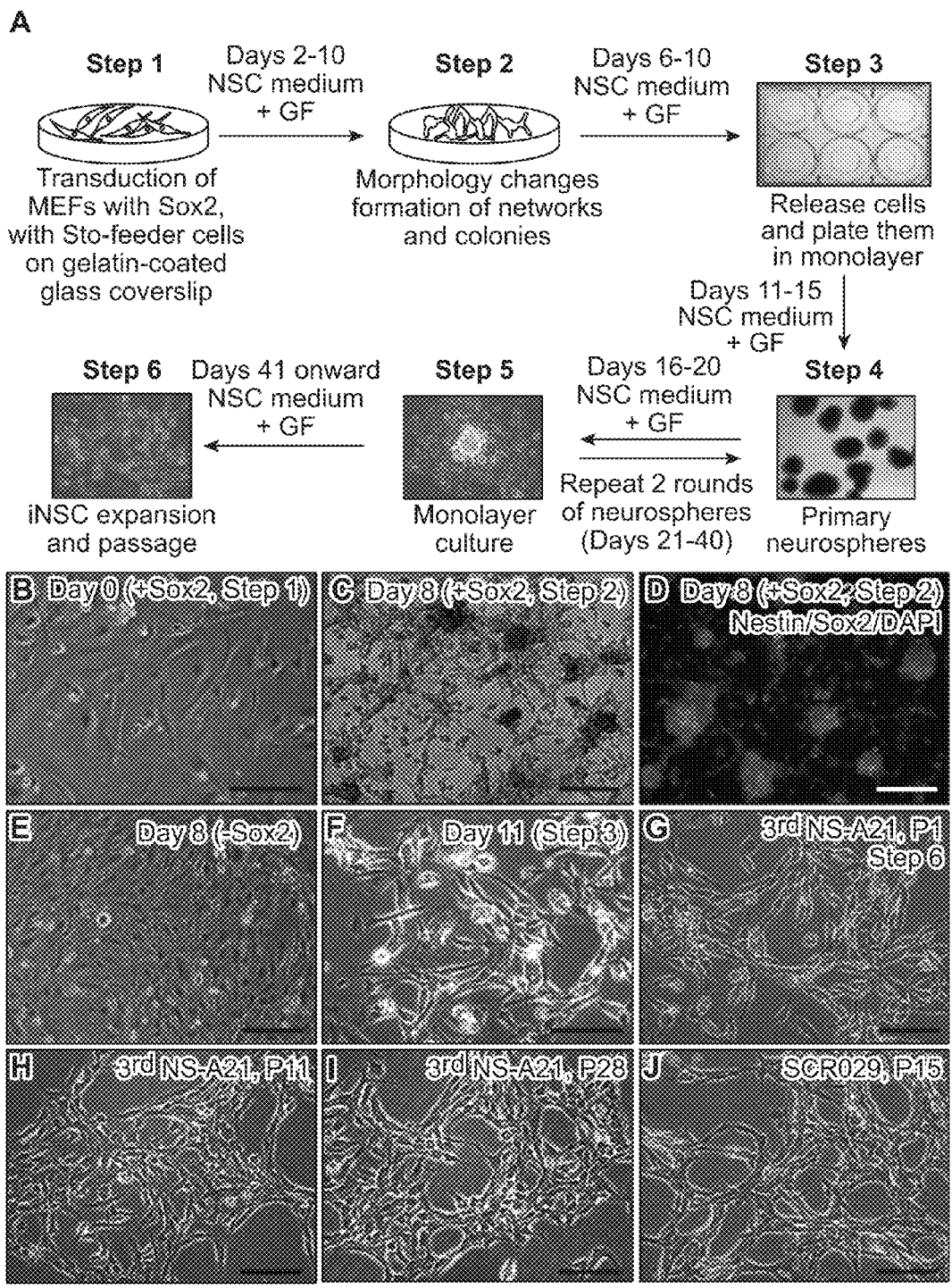
FIGS. 1A-J depict generation of iNSCs from mouse fibroblasts.

As used herein, the term "neural stem cell" (NSC) refers to an undifferentiated neural cell that can proliferate, self-renew, and differentiate into the main adult neural cells of the brain. NSCs are capable of self-maintenance (self-renewal), meaning that with each cell division, one daughter cell will also be a stem cell. The non-stem cell progeny of NSCs are termed neural progenitor cells. Neural progenitors cells generated from a single multipotent NSC are capable of differentiating into neurons, astrocytes (type I and type II), and oligodendrocytes. Hence, NSCs are "multipotent" because their progeny have multiple neural cell fates. Thus, NSCs can be functionally defined as a cell with the ability to: 1) proliferate, 2) self-renew, and 3) produce functional progeny that can differentiate into the three main cell types found in the central nervous system: neurons, astrocytes and oligodendrocytes.

As used herein, the terms "neural progenitor cell" or "neural precursor cell" refer to a cell that can generate progeny such as neuronal cells (e.g., neuronal precursors or mature neurons), glial precursors, mature astrocytes, or mature oligodendrocytes. Typically, the cells express some of the phenotypic markers that are characteristic of the neural lineage. A "neuronal progenitor cell" or "neuronal precursor cell" is a cell that can generate progeny that are mature neurons. These cells may or may not also have the capability to generate glial cells.

As used herein, the term "transcription factor" refers to a protein that targets a specific DNA sequence(s) in order to promote or block transcription of genetic information, encoded in DNA, into RNA.

As used herein, the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated genetically modified host cell can be present in a mixed population of genetically modified host cells, or in a mixed population comprising genetically modified host cells and host cells that are not genetically modified. For example, an isolated genetically modified host cell can be present in a mixed population of genetically modified host cells in vitro, or in a mixed in vitro population comprising genetically modified host cells and host cells that are not genetically modified.

A "host cell," as used herein, denotes an in vivo or in vitro cell (e.g., a eukaryotic cell cultured as a unicellular entity), which eukaryotic cell can be, or has been, used as recipients for a nucleic acid (e.g., an exogenous nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

The term "genetic modification," as used herein, refers to a permanent or transient genetic change induced in a cell following introduction of a nucleic acid (i.e., exogenous nucleic acid) into the cell. Genetic change ("modification") can be accomplished by incorporation of exogenous nucleic acid into the genome of the host cell, or by transient or stable maintenance of the exogenous nucleic acid as an extrachromosomal element. Where the cell is a eukaryotic cell, a permanent genetic change can be achieved by introduction of exogenous nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an induced neural stem cell" includes a plurality of such cells and reference to "the Sox2 polypeptide" includes reference to one or more Sox2 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of generating neural stem cells from differentiated somatic cells. The present disclosure also provides induced neural stem cells generated using a subject method, as well as differentiated cells generated from a subject induced neural stem cell. A subject neural stem cell, as well as differentiated cells derived from a subject neural stem cell, is useful in various applications, which are also provided in the present disclosure.

Methods of Generating Neural Stem Cells

The present disclosure provides in vitro methods of generating induced neural stem cells (iNSCs) from somatic cells. The methods generally involve: a) introducing a single exogenous induction factor (e.g., a Sox2 polypeptide) into a somatic cell; and b) culturing the exogenous induction factor-modified somatic cell on a protein-coated solid substrate, where the solid substrate is not a plastic substrate, such that a multipotent neural stem cell is generated. In some embodiments, the methods generally involve: a) introducing an exogenous Sox2 polypeptide into a somatic cell, to generate an exogenous Sox2-modified somatic cell that comprises exogenous Sox polypeptide; and b) culturing the exogenous Sox2-modified somatic cell on a protein-coated solid substrate, where the solid substrate is not a plastic substrate, such that a multipotent neural stem cell is generated. In many embodiments, a plurality of iNSCs are generated using a subject method.

It has been found that introduction of a single exogenous polypeptide (exogenous induction factor), together with culturing on a protein-coated solid substrate, where the substrate (e.g., the surface of the substrate on which cells are cultured) is not plastic, is sufficient to reprogram a somatic cell to become a NSC. Thus, a somatic cell can be reprogrammed to become a NSC without the need for introducing any other induction factor (e.g., any other exogenous polypeptide) into the somatic cell. For example, a subject method does not require and does not involve introducing into a somatic cell any of an exogenous Oct-3/4 polypeptide, an exogenous c-Myc polypeptide, an exogenous Klf4 polypeptide, an exogenous Nanog polypeptide, or an exogenous Lin28 polypeptide.

Oct-3/4 polypeptides, c-Myc polypeptides, and Klf4 polypeptides, are known in the art and are described in, e.g., U.S. Patent Publication No. 2009/0191159. Nanog polypeptides and Lin28 polypeptides are known in the art and are described in, e.g., U.S. Patent Publication No. 2009/0047263. See also the following GenBank Accession Nos.: 1) GenBank Accession Nos. NP_002692, NP_001108427; NP_001093427; NP_001009178; and NP_038661 for Oct-3/4; 2) GenBank Accession Nos. NP_004226, NP_001017280, NP_057354, AAP36222, NP_034767, and NP_446165 for Klf4 and Klf4 family members; 3) GenBank Accession Nos. NP_002458, NP_001005154, NP_036735, NP_034979, P0C0N9, and NP_001026123 for c-Myc; 4) GenBank Accession Nos. AAP49529 and BAC76999, for Nanog; and 5) GenBank Accession Nos. AAH28566 and NP_078950, for Lin28. A subject method does not involved forced expression of a polypeptide comprising an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to an Oct-3/4, a c-Myc, a Klf4, a Nanog, or a Lin28 polypeptide.

A subject method can involve forced expression of a Sox2 polypeptide in a somatic cell. Forced expression of a polypeptide can include introducing an expression vectors encoding polypeptides of interest into cells, introducing exogenous purified polypeptides of interest into cells, or contacting cells with a non-naturally occurring reagent that induces expression of an endogenous gene encoding a polypeptide of interest. A subject method does not involved forced expression of any polypeptide other than Sox2 in the somatic cell. Thus, e.g., a subject method does not involved forced expression of any of an Oct-3/4 polypeptide, a c-Myc polypeptide, a Klf4 polypeptide, a Nanog polypeptide, or a Lin28 polypeptide.

A subject NSC (also referred to as an "induced neural stem cell" or a "multipotent neural stem cell") exhibits one or more of the following properties: 1) expression of Nestin; 2) expression of Sox2; 3) expression of Musashi1; 4) ability to undergo self-renewal, either as a monolayer or in suspension cultures as neurospheres; 5) ability to differentiate into neurons, specific subtypes of neurons, astrocytes, and oligodendrocytes; and 6) morphological characteristics typical for NSCs. A subject iNSC can also express CD133 and Vimentin. Nestin, Sox2, and Musashi1 are well described in the literature as hallmark genes expressed in NSCs. See, e.g., GenBank Accession Nos. NP_006608, CAA46780, and CAI16338 for Nestin. For Nestin, see also, e.g., Dahlstrand et al. (1992) *J. Cell Sci.* 103:589. An example of a Sox2 amino acid sequence is provided in FIG. 8A. For Musashi1, see, e.g., GenBank Accession No. BAB69769; and Shu et al. (2002) *Biochem. Biophys. Res. Comm.* 293:150.

A subject iNSC is generally negative for markers that identify mature neurons, astrocytes, and oligodendrocytes. Thus, e.g., a subject iNSC is generally microtubule-associated protein-2 (MAP2) negative, neuron-specific nuclear protein (NeuN) negative, Tau negative, S100β negative, oligodendrocyte marker O4 negative, and oligodendrocyte lineage transcription factor Olig2 negative. These markers of mature neural markers are well described in the literature. For MAP2, see, e.g., GenBank Accession Nos. AAA59552, AAB48098, AAI43246, and AAH38857. For NeuN, see, e.g., Wolf et al. (1996) *J. Histochem. & Cytochem.* 44:1167. For S100β, see, e.g., GenBank Accession Nos. NP_006263.1 (*H. sapiens* S100β); NP_033141 (*Mus musculus* S100β); CAG46920.1 (*Homo sapiens* S100β); and see also, Allore et al. (1990) *J. Biol. Chem.* 265:15537. For O4, see, e.g., Schachner et al. (1981) *Dev. Biol.* 83:328; Bansal et al. (1989(*J. Neurosci. Res.* 24:548; and Bansal and Pfeiffer (1989) *Proc. Natl. Acad. Sci. USA* 86:6181. For Olig2, see, e.g., Lu et al. (2001) *Proc. Natl. Acad. Sci. USA* 98:10851; Ligon et al. (2004) *J. Neuropathol. Exp. Neurol.* 63:499.

Whether a subject iNSC expresses particular markers and/or lacks expression of particular markers, can be readily determined using well-established assays. For example, cell-specific markers and differentiation-specific markers can be detected using any suitable immunological technique, such as fluorescence-activated cell sorting (FACS) for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen (a marker) by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of cell-specific and differentiation-specific gene products can also be detected at the mRNA level by Northern blot analysis, dot-blot hybridization analysis, or by a reverse transcription polymerase chain reaction (RT-PCR) using sequence-specific primers in standard amplification methods. Expression at the mRNA level is said to be "detectable" according to a standard assay if the performance of the assay on cell samples according to standard procedures in a typical controlled experiment results in clearly discernable hybridization or amplification product. Expression of cell-specific (e.g., neural stem cell-specific) and differentiation-specific markers as detected at the protein or mRNA level is considered positive if the level is at least 2-fold, or more than 10- or 50-fold above that of a control cell, such as a pluripotent embryonic stem cell, a fibroblast, or other unrelated cell type.

Whether a subject NSC has the ability to differentiate into a neuron, an astrocyte, or an oligodendrocyte can be readily determined by inducing differentiation of the NSC. Methods of inducing differentiation of a NSC to become an astrocyte, an oligodendrocyte, or a neuron, are discussed in detail below and a number of such methods are known in the art.

One of the characteristics of stem cells is their ability to proliferate continuously without undergoing senescence. Accordingly, a subject induced NSC can be passaged continuously in vitro. For example, a subject induced NSC can be passaged for at least about 30 to at least about 100 times in vitro, e.g., about 33, 35, 40, 45, 51, 56, 60, 68, 75, 80, 90, 93, 100, or any other number of passages from at least about 30 to at least about 100 passages.

A subject induced NSC can proliferate for a period of from about 30 days to about 500 days from introduction of an exogenous Sox2 polypeptide into a host somatic cell, e.g., 40 days, 50 days, 60 days, 70 days, 80 days, 100 days, 150 days, 180 days, 200 days, 250 days, 300 days, 400 days, 450 days or any other period from about 30 days to about 500 days from introduction of an exogenous Sox2 polypeptide into a host somatic cell.

A subject induced NSC retains a normal karyotype, even after multiple in vitro passages. For example, a subject induced NSC exhibits diploidy and a normal, stable karyotype, e.g., stable after the cells have been passaged for at least one month, at least 4 months, at least 6 months, at least 10 months, or at least one year in vitro. A number of karotype analysis methods are known in the art. In some embodiments, the karyotype analysis method is multicolor fluorescence in situ hybridization (FISH) as described in, e.g., Bayani et al. (2004) Curr. Protoc. Cell Biol. Chapter 22:Unit 22.5. Another suitable method is a molecular karyotype analysis as described in, e.g., Vermeesch et al. (2007) *Eur. J. Hum. Genet.* 15(11):1105-1114.

A subject induced NSC does not form cancerous cells in vitro or in vitro. Thus, e.g., a subject induced NSC exhibits normal, controlled cell proliferation.

Sox2 Polypeptides

Sox2 (sex-determining region Y-box 2) polypeptides are known in the art, and any Sox2 polypeptide that retains Sox2 activity is suitable for use. A Sox2 polypeptide that retains Sox2 activity is also referred to as a "biologically active Sox2 polypeptide." A suitable Sox2 polypeptide that retains Sox2 activity is one that: (i) includes a DNA binding domain (DBD) that binds to the human nanog gene Sox element: 5'-TACAATG-3'; and (ii) is capable of transactivating a promoter comprising one or more nanog gene promoter Sox elements. See, e.g., Kuroda et al. (2005) *Mol. Cell. Biol.* 25(6):2475-2485. Sox2 amino acid sequences can be found in, e.g., GenBank Accession Nos: NP_003097, NP_001098933, NP_035573, ACA58281, BAA09168, NP_001032751, and NP_648694. In some embodiments, a suitable Sox2 polypeptide retains Sox2 activity and comprises an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to the Sox2 amino acid sequence depicted in FIG. 8A. In some embodiments, a Sox2 polypeptide comprises a protein transduction domain, as described below.

Introduction of Exogenous Sox2 Polypeptide into a Somatic Cell

In some embodiments, introduction of an exogenous Sox2 polypeptide into a somatic cell is achieved by contacting the somatic cell with the exogenous Sox2 polypeptide, wherein the exogenous Sox2 polypeptide is taken up into the cell.

In some embodiments, an exogenous Sox2 polypeptide comprises a protein transduction domain, e.g., an exogenous Sox2 polypeptide is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a Sox2 polypeptide. In some embodiments, a PTD is covalently linked to the carboxyl terminus of a Sox2 polypeptide.

Exemplary protein transduction domains include but are not limited to a minimal undecapeptide protein transduction domain (corresponding to residues 47-57 of HIV-1 TAT comprising YGRKKRRQRRR; SEQ ID NO:3); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an *Drosophila* Antennapedia protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:4); Transportan GWTLNSAGYLLGKINLKALAALAKKIL (SEQ ID NO:5); KALAWEAKLAKALAKALAKHLAKALAKALKCEA (SEQ ID NO:6); and RQIKIWFQNRRMKWKK (SEQ ID NO:7). Exemplary PTDs include but are not limited to, YGRKKRRQRRR (SEQ ID NO:3), RKKRRQRRR (SEQ ID NO:8); an arginine homopolymer of from 3 arginine residues to 50 arginine residues; Exemplary PTD domain amino acid sequences include, but are not limited to, any of the following: YGRKKRRQRRR (SEQ ID NO:3); RKKRRQRR (SEQ ID NO:8); YARAAARQARA (SEQ ID NO:9); THRLPRRRRRR (SEQ ID NO:10); and GGRRARRRRRR (SEQ ID NO:11).

In some embodiments, an exogenous Sox2 polypeptide comprises an arginine homopolymer of from 3 arginine residues to 50 arginine residues, e.g., from 3 to 6 arginine residues, from 6 to 10 arginine residues, from 10 to 20 arginine residues, from 20 to 30 arginine residues, from 30 to 40 arginine residues, or from 40 to 50 arginine residues. In some embodiments, an exogenous Sox2 polypeptide comprises six Arg residues covalently linked (e.g., by a peptide bond) at the amino terminus of the Sox2 polypeptide. In some embodiments, an exogenous Sox2 polypeptide comprises six Arg residues covalently linked (e.g., by a peptide bond) at the carboxyl terminus of the Sox2 polypeptide.

The exogenous Sox2 polypeptide introduced into a host somatic cell can be purified, e.g., at least about 75% pure, at least about 80% pure, at least about 85% pure, at least about 90% pure, at least about 95% pure, at least about 98% pure, at least about 99% pure, or more than 99% pure, e.g., free of proteins other than Sox2 polypeptide and free of macromolecules other than Sox2 polypeptides.

Genetic Modification of a Somatic Cell

In some embodiments, introduction of an exogenous Sox2 polypeptide into a somatic cell is achieved by genetic modification of the somatic cell with an exogenous nucleic acid comprising a nucleotide sequence encoding a Sox2 polypeptide. An exogenous nucleic acid comprising a nucleotide sequence encoding a Sox2 polypeptide is also referred to herein as "an exogenous Sox2 nucleic acid."

The exogenous Sox2 nucleic acid can be a recombinant expression vector, where suitable vectors include, e.g., recombinant retroviruses, lentiviruses, and adenoviruses; retroviral expression vectors, lentiviral expression vectors, nucleic acid expression vectors, and plasmid expression vectors. In some cases, the exogenous Sox2 nucleic acid is integrated into the genome of a host somatic cell and its progeny. In other cases, the exogenous Sox2 nucleic acid persists in an episomal state in the host somatic cell and its progeny. In some cases, an endogenous, natural version of the Sox2-encoding nucleic acid may already exist in the cell but an additional "exogenous gene" is added to the host somatic cell to increase Sox2 polypeptide expression. In other cases, the exogenous Sox2 nucleic acid encodes a Sox2 polypeptide having an amino acid sequence that differs by one or more amino acids from a Sox2 polypeptide encoded by an endogenous Sox-encoding nucleic acid within the host somatic cell.

In some embodiments, an exogenous Sox2 nucleic acid is introduced into a single somatic cell (e.g., a single somatic host cell) in vitro. In other embodiments, an exogenous Sox2 nucleic acid is introduced into a population of somatic cells (e.g., a population of host somatic cells) in vitro.

Where a population of somatic cells is genetically modified with an exogenous Sox2 nucleic acid, the exogenous Sox2 nucleic acid can be introduced into greater than 20% of the total population of cells somatic cells, e.g., 25%, 30%, 35%, 40%, 44%, 50%, 57%, 62%, 70%, 74%, 75%, 80%, 90%, or other percent of cells greater than 20%.

Examples of suitable mammalian expression vectors include, but are not limited to: recombinant viruses, nucleic acid vectors, such as plasmids, bacterial artificial chromosomes, yeast artificial chromosomes, human artificial chromosomes, cDNA, cRNA, and polymerase chain reaction (PCR) product expression cassettes. Examples of suitable promoters for driving expression of a Sox2-encoding nucleotide sequence include, but are not limited to, retroviral long terminal repeat (LTR) elements; constitutive promoters such as CMV, HSV1-TK, SV40, EF-1α, β-actin; phosphoglycerol kinase (PGK), and inducible promoters, such as those containing Tet-operator elements. In some cases, the mammalian expression vector encodes, in addition to an exogenous Sox2 polypeptide, a marker gene that facilitates identification or selection of cells that have been transfected or infected. Examples of marker genes include, but are not limited to, genes encoding fluorescent proteins, e.g., enhanced green fluorescent protein, DS-Red, yellow fluorescent protein, and cyanofluorescent protein; and genes encoding proteins conferring resistance to a selection agent, e.g., the neomycin resistance gene, and the blasticidin resistance gene.

Examples of recombinant viruses include, but are not limited, to retroviruses (including lentiviruses); adenoviruses; and adeno-associated viruses. An example of a suitable recombinant retrovirus is murine moloney leukemia virus (MMLV); however, other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus, see, e.g., U.S. Pat. No. 6,333,195.

In other cases, the recombinant retrovirus is a lentivirus (e.g., Human Immunodeficiency Virus-1 (HIV-1); Simian Immunodeficiency Virus (SIV); or Feline Immunodeficiency Virus (FIV)), See, e.g., Johnston et al., (1999), Journal of Virology, 73(6):4991-5000 (FIV); Negre D et al., (2002), Current Topics in Microbiology and Immunology, 261:53-74 (SIV); Naldini et al., (1996), Science, 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, e.g., ecotropic env, which aids entry into cells of the original host species.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al., (1994), Methods Cell Biol., Pt A:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al., (2000), Gene Therapy, 7:1063-1066; Onishi et al., (1996), Experimental Hematology, 24:324-329; U.S. Pat. No. 6,995, 009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1α, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. See e.g., Onishi et al. (1996) Experimental Hematology 24:324-329. In some cases, the retroviral construct is a self-inactivating lentiviral vector (SIN) vector, see, e.g., Miyoshi et al. (1998) J. Virol. 72(10):8150-8157. In some cases, the retroviral construct is LL-CG, LS-CG, CL-CG, CS-CG, CLG or MFG. Miyoshi et al. (1998) J. Virol. 72(10):8150-8157; Onishi et al. (1996) Experimental Hematology 24:324-329; Riviere et al. (1995) Proc. Natl. Acad. Sci. USA 92:6733-6737. Virus vector plasmids (or constructs), include: pMXs, pMxs-IB, pMXs-puro, pMXs-neo (pMXs-IB is a vector carrying the blasticidin-resistant gene in stead of the puromycin-resistant gene of pMXs-puro) Kimatura et al. (2003) Experimental Hematology 31: 1007-1014; MFG Riviere et al. (1995) Proc. Natl. Acad. Sci. USA 92:6733-6737; pBabePuro; Morgenstern et al. (1990) Nucleic Acids Research 18:3587-3596; LL-CG, CL-CG, CS-CG, CLG Miyoshi et al. (1998) J. Virol. 72:8150-8157 and the like as the retrovirus system; and pAdexl Kanegae et al. (1995) Nucleic Acids Research 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al. (1990) Nucleic Acids Research 18:3587-3596.

Methods of producing recombinant viruses from packaging cells and their uses are well established; see, e.g., U.S. Pat. Nos. 5,834,256; 6,910,434; 5,591,624; 5,817,491; 7,070,994; and 6,995,009, incorporated herein by reference. Many methods begin with the introduction of a viral construct into a packaging cell line. The viral construct may be introduced by any method known in the art, including but not limited to: a calcium phosphate method, a lipofection method (Feigner et al. (1987) Proc. Natl. Acad. Sci. U.S.A. 84:7413-7417), an electroporation method, microinjection, Fugene transfection, and the like, and any method described herein.

A nucleic acid construct can be introduced into a cell using a variety of well known techniques, such as non-viral based transfection of the cell. In an exemplary aspect the construct is incorporated into a vector and introduced into a host cell. Introduction into the cell may be performed by any non-viral based transfection known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include transfection reagents such as Lipofectamine™, Dojindo Hilymax™ Fugene™, jetPEI™, Effectene™, and DreamFect™.

Somatic Cells

An exogenous Sox2 polypeptide can be introduced into a single somatic cell in vitro, or can be introduced into a population of somatic cells in vitro. The somatic cell can be, e.g., a mammalian cell, e.g., a murine cell (e.g., a mouse cell; a rat cell), a human cell, a non-human primate cell, a somatic cell of an ungulate (equine, bovine, ovine, etc.), a feline cell, a canine cell, and the like.

A multipotent NSC can be induced from a wide variety of mammalian somatic cells. Examples of suitable mammalian cells include, but are not limited to: fibroblasts (including dermal fibroblasts, human foreskin fibroblasts, etc.), bone marrow-derived mononuclear cells, skeletal muscle cells, adipose cells, peripheral blood mononuclear cells, macrophages, hepatocytes, keratinocytes, oral keratinocytes, hair follicle dermal cells, gastric epithelial cells, lung epithelial cells, synovial cells, kidney cells, skin epithelial cells, and osteoblasts.

A somatic cell can also originate from many different types of tissue, e.g., bone marrow, skin (e.g., dermis, epidermis), muscle, adipose tissue, peripheral blood, foreskin, skeletal muscle, or smooth muscle. The cells can also be derived from neonatal tissue, including, but not limited to: umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.

A somatic cell can be obtained from any of a variety of mammals, including, e.g., humans, non-human primates, murines (e.g., mice, rats), ungulates (e.g., bovines, equines, ovines, caprines, etc.), felines, canines, etc.

A somatic cell can be obtained from neonatal or post-natal tissue collected from a subject within the period from birth, including cesarean birth, to death. For example, the tissue may be from a subject who is >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years old.

The cells can be from non-embryonic tissue, e.g., at a stage of development later than the embryonic stage. In other cases, the cells may be derived from an embryo. In some cases, the cells may be from tissue at a stage of development later than the fetal stage. In other cases, the cells may be derived from a fetus.

The cells to be induced or reprogrammed can be obtained from a single cell or a population of cells. The population may be homogeneous or heterogeneous. The cells can be a population of cells found in a cellular sample, e.g., a biopsy or blood sample. The cells can be a population of human cells present in a cellular sample.

Methods for obtaining human somatic cells are well established, as described in, e.g., Schantz and Ng (2004), A Manual for Primary Human Cell Culture, World Scientific Publishing Co., Pte, Ltd. In some cases, the methods include obtaining a cellular sample, e.g., by a biopsy (e.g., a skin sample), blood draw, or alveolar or other pulmonary lavage. It is to be understood that initial plating densities of cells prepared from a tissue can vary, due to a variety of factors, e.g., expected viability or adherence of cells from that particular tissue.

After collection, tissue or cellular samples can be cultured in any medium suitable for the specific cells or tissue collected. Some representative media that the tissue or cells can be cultured in include but are not limited to: multipotent adult progenitor cell (MAPC) medium; FBM (manufactured by Lonza); Embryonic Stem cell (ES) ES medium; Mesenchymal Stem Cell Growth Medium (MSCGM) (manufactured by Lonza); MCDB202 modified medium; Endothelial Cell Medium kit-2 (EBM2) (manufactured by Lonza); Iscove's Modified Dulbecco's Medium (IMDM) (Sigma); Minimum Essential Medium (MEM); Dulbecco's Modified Eagle Medium (DMEM); MEF-conditioned ES (MC-ES); and mTeSR (available, e.g., from StemCell Technologies, Vancouver, Canada), See, e.g., Ludwig et al., (2006), Nat. Biotechnol., 24(2):185-187. In other cases, alternative culture conditions for growth of human ES cells are used, as described in, e.g., Skottman et al., (2006), Reproduction, 132(5):691-698.

Solid Substrate

Suitable solid substrates (e.g., the surface of the solid substrate on which a cell is cultured) generally comprise materials other than plastic, e.g., other than polystyrene, polycarbonate, polyvinyl chloride, polyvinylidene fluoride, polyvinyl acetate, polyvinyl pyrrolidone, polyacrylonitrile, polyacrylamide, polymethyl methacrylate, polytetrafluoroethylene, polyethylene, polypropylene, and polycarbonate, divinylbenzene styrene-based polymers, and the like. Suitable solid substrates include, but are not limited to, glass coverslips and microtiter wells or sheets produced with any of the following materials: controlled pore glass, functionalized glass, ceramics, silica, silica-based materials, celluloses (such as nitrocellulose), cellulosic polymers, polysaccharides, and metals.

The solid substrate is coated with a protein. Suitable proteins include, but are not limited to, gelatin, fibronectin, albumin, collagen, elastin, laminin, elastin, poly-lysine, poly-ornithine, a polypeptide comprising one or more Arg-Gly-Asp (RGD) sequences; and the like. Suitable proteins include extracellular matrix (ECM) proteins (e.g., naturally-occurring ECM proteins; synthetic ECM proteins; etc.); and the like. The protein can be naturally occurring, recombinant, or synthetic. The protein can be modified with, e.g., heparan sulfate, chondroitin sulfate, keratan sulfate, hyaluronic acid, and the like.

In some embodiments, the protein coating includes only one protein, e.g., the coating is a homogeneous composition comprising a single species of protein. For example, in some embodiments, the protein coating comprises only gelatin and no other protein. The protein coating can also comprise two or more different proteins, e.g., the protein coating can comprise a mixture of albumin and collagen, a mixture of collagen and elastin, a mixture of gelatin and fibronectin, etc.

The protein, or mixture of proteins, is coated onto the solid substrate at a concentration of from about 1 µg/m to about 500 µg/ml, e.g., at a concentration of from about 1 µg/m to about 5 µg/ml, from about 5 µg/m to about 15 µg/ml, from about 15 µg/m to about 20 µg/ml, from about 20 µg/m to about 25 µg/ml, from about 25 µg/m to about 30 µg/ml, from about 30 µg/m to about 50 µg/ml, from about 50 µg/m to about 100 µg/ml, from about 100 µg/m to about 200 µg/ml, from about 200 µg/m to about 300 µg/ml, from about 300 µg/m to about 400 µg/ml, or from about 400 µg/m to about 500 µg/ml.

Culture Conditions

Once an exogenous Sox2 polypeptide has been introduced into a somatic cell, the somatic cell is cultured in a liquid medium on a protein-coated solid substrate. The liquid culture medium can be any of a variety of standard culture media, where suitable culture media include, but are not limited to, Iscove's Modified Dulbecco's Medium (IMDM) (Sigma); Minimum Essential Medium (MEM); Dulbecco's Modified Eagle Medium (DMEM); mouse embryonic fibroblast-conditioned medium (MEF-conditioned medium); multipotent adult progenitor cell (MAPC) medium; and the like. MAPC (2% fetal bovine serum (FBS)) medium may comprise: 60% Dulbecco's Modified Eagle's Medium-low glucose, 40% MCDB 201, Insulin Transferrin Selenium supplement, (0.01 mg/ml insulin; 0.0055 mg/ml transferrin; 0.005 µg/m sodium selenite), 1× linolenic acid albumin (1 mg/mL albumin; 2 moles linolenic acid/mole albumin), 1 nM dexamethasone, 2% fetal bovine serum, 1 nM dexamethasone, $10^{-4}$ M ascorbic acid, and 10 µg/m gentamycin. Cells may be cultured in medium supplemented with a particular serum. In some embodiments, the serum is fetal bovine serum (FBS). The serum can also be fetal calf serum (FCS). In some cases, the serum may be human serum (e.g., human AB serum). Mixtures of different sera may also be used, e.g. mixture of FBS and Human AB, FBS and FCS, or FCS and Human AB.

Suitable liquid culture media also include NeuroCult® liquid culture medium; Stemline™ neural stem cell expansion medium; a culture medium as described in Swistowski et al. (2009) *PLoS One* 4:e6233; Neural Stem Cell Basal Medium (Millipore); and the like.

Suitable conditions for in vitro culturing include physiological conditions. The pH of the culture medium should be close to physiological pH, e.g., between pH 6 and pH 8, e.g., between about pH 7 to pH 7.8, e.g., pH 7.4. Physiological temperatures range between about 30° C. and about 40° C. Cells are cultured at temperatures from about 32° C. to about 38° C., e.g., between about 35° C. and about 37° C.

In some embodiments, the neural stem cells are cultured in serum-free media containing epidermal growth factor (EGF) or an analog of EGF (such as amphiregulin), or transforming growth factor alpha (TGF-α), as the mitogen for proliferation. See, e.g., WO 93/01275, WO 94/16718. Further, basic fibroblast growth factor (bFGF) can be used, either alone, or in combination with EGF, to enhance long term neural stem cell survival. A culture medium (e.g., a serum-free culture medium) comprising EGF, bFGF, and heparin can be used.

The protein-coated solid substrate can be further modified to include a feeder layer of cells. If present, the feeder layer is inactivated, e.g., by irradiation or mitomycin treatment. For example, the cells may be cultured on a layer, or carpet, of murine embryonic fibroblasts (MEFs), where the MEFS are inactivated (e.g., irradiated or mitomycin-treated MEFs), e.g., American Type Culture Collection (ATCC) Nos. CRL-2752, SCRC-1008, CRL-2214, SCRC-1040, etc. Other suitable feeder cells include STO cells (ATCC CRL-1503), including irradiated or mitomycin-C-treated STO cells; SNL cells (see, e.g., McMahon and Bradley (1990) *Cell* 62:1073), including irradiated or mitomycin-C-treated SNL cells; STO-SNL/2 cells (ATCC CRL-2225), including irradiated or mitomycin-C-treated STO-SNL/2 cells; and the like. The feeder layer can produce various factors, e.g., leukemia inhibitory factor (LIF).

Also suitable for use are human feeder cells, e.g., human embryonic lung fibroblasts, human adult uterine endometrial cells (hUECs), human adult breast parenchymal cells (hB-PCs), embryonic fibroblasts (hEFs), and the like. For human feeder cells, see, e.g., Amit et al. (2003) *Biol. Reprod.* 68:2150; and Lee et al. (2004) *Reproduction* 128:727. Human foreskin fibroblasts can also be used as feeder cells. If human cells are used as feeder cells, the human cells can be mitomycin-C treated or irradiated.

Purification

An iNSC obtained as described above will in some embodiments be present in a mixed cell population comprising the NSC and other, non-NSCs, where possible non-NSCs include: i) host somatic cells that failed to be fully reprogrammed to become NSCs; and ii) non-NSCs present in the original cell population.

In some embodiments, an induced NSC will be purified from a mixed cell population, e.g., separated from non-NSCs that may be present in a mixed cell population comprising a subject NSC. For example, an NSC can be sorted based on phenotypic features characteristic of NSCs. Sorting can involve contacting each cell with an antibody or ligand that binds to a marker characteristic of an NSC, followed by separation of the specifically recognized cells from other cells in the population. One method is immunopanning, in which specific antibody is coupled to a solid surface. The cells are contacted with the surface, and cells not expressing the marker are washed away. The bound cells are then recovered by more vigorous elution. Variations of this are affinity chromatography and antibody-mediated magnetic cell sorting. In an exemplary sorting procedure, the cells are contacted with a specific primary antibody, and then captured with a secondary anti-immunoglobulin reagent bound to a magnetic bead. The adherent cells are then recovered by collecting the beads in a magnetic field.

For example, cells selected positively for expression of nestin can provide a population that is 60%, 70%, 80%, 90%, or greater than 90% (e.g., 95%, 98%, 99%, or greater than 99%), nestin positive.

Separation of iNSCs from non-NSCs present in a mixed cell population comprising iNSCs and non-NSCs results in a purified iNSC cell population, where at least about 80%, at least about 85%, at least about 90%, at least about 95%, at least about 98%, at least about 99%, or more than 99%, of the cells of the purified NSC population are iNSCs.

A subject iNSC can be amplified, e.g., to obtain a purified induced NSC population comprising from about $10^3$ to about $10^8$ or more purified induced NSCs, e.g., from about $10^3$ purified induced NSCs to about $10^4$ purified induced NSCs, from about $10^4$ purified induced NSCs to about $10^5$ purified induced NSCs, from about $10^5$ purified induced NSCs to abut $10^6$ purified induced NSCs, from about $10^6$ purified induced NSCs to about $10^7$ purified induced NSCs, from about $10^7$ purified induced NSCs to about $10^8$ purified induced NSCs, or more than $10^8$ purified induced NSCs.

A subject iNSC (or a population of purified iNSCs) can be stored. For example, a subject iNSC, or a population of purified iNSCs, can be cryopreserved, using well-established methods.

Compositions Comprising NSCs

The present disclosure provides a composition comprising a subject iNSC (or a population of iNSCs, e.g., a population of purified iNSCs).

A subject composition various components in addition to the iNSCs. For example, a subject composition can include a subject iNSC(s) and a culture medium. In some cases, the culture medium comprises one or more growth factors. In some embodiments, the culture medium is a serum-free culture medium. In some cases, the composition comprises iNSCs and a cryopreservative agent, e.g., a cryopreservation medium.

A subject composition can include a subject iNSC and a matrix, e.g., a matrix component. Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

The cell density in a subject iNSC/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Inducing Differentiation of an iNSC

A subject iNSC can be induced in vitro to become a neuron, an astrocyte, or an oligodendrocyte. Methods of inducing differentiation of a NSC to generate a neuron, an astrocyte, or an oligodendrocyte, are known in the art, and any method, including any known method, can be used.

Neurons

Under the proper culture conditions, a subject iNSC can be induced to express specific neural genes, such as for example, genes of the mid-brain dopaminergic lineage, e.g., Nurr1 and Ptx3. A subject iNSC can be induced to express mid-brain dopaminergic genes by culturing a subject iNSC in glial cell-conditioned media comprising the mitogenic factors epidermal growth factor (EGF), basic fibroblast growth factor (bFGF), and leukemia inhibitory factor (LIF).

A subject iNSC can be induced to differentiate into tyrosine hydroxylase (TH)-expressing neurons. TH is a known marker for dopaminergic neurons. In one embodiment of the invention, a subject TH-expressing neuron is derived by: (a) inducing mid-brain dopaminergic gene expression in a subject iNSC to differentiate to neurons; and (b) culturing the neurons in media conditioned to induce the neurons to express TH. In order to induce TH expression, the neurons are cultured with at least one mitogenic factor in glial conditioned media. The at least one mitogenic growth factor can include a member of the fibroblastic growth factor (FGF) family, e.g., FGF1, FGF2 (also known as bFGF or basic FGF), FGF3, FGF4, FGF5, FGF6, FGF8, FGF9, and FGF 10 to FGF20. In one embodiment, the at least one mitogenic growth factor is bFGF. In another embodiment, the mitogenic growth factors include bFGF, and one or both of EGF and LIF.

In some embodiments, a subject iNSC is differentiated into a motor neuron, where the motor neuron is positive for HB9. In some embodiments, a subject iNSC is differentiated into a GABAergic neuron, where the GABAergic neuron is positive for GAD67. In some embodiments, a subject induced NSC is differentiated into a dopaminergic neuron, where the dopaminergic neuron is TH positive.

Neurons may be identified by expression of neuronal markers Tuj1 (β-III-tubulin); MAP-2 (microtubule associated protein 2, other MAP genes such as MAP-1 or -5 may also be used); anti-axonal growth clones; ChAT (choline acetyltransferase); CgA (anti-chromagranin A); DARRP (dopamine and cAMP-regulated phosphoprotein); DAT (dopamine transporter); GAD (glutamic acid decarboxylase); GAP (growth associated protein); anti-HuC protein; anti-HuD protein; α-internexin; NeuN (neuron-specific nuclear protein); NF (neurofilament); NGF (nerve growth factor); γ-SE (neuron specific enolase); peripherin; PH8; PGP (protein gene product); SERT (serotonin transporter); synapsin; Tau (neurofibrillary tangle protein); anti-Thy-1; TRK (tyrosine kinase receptor); TRH (tryptophan hydroxylase); anti-TUC protein; TH (tyrosine hydroxylase); VRL (vanilloid receptor like protein); VGAT (vesicular GABA transporter), VGLUT (vesicular glutamate transporter).

A neuron generated by inducing differentiation of a subject NSC can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored. The cells can also be subjected to standard patch-clamp techniques, to determine whether there is evidence for an action potential, and what the lag time is between applied potential and response. Differentiation of a subject NSC can generate cultures that contain subpopulations that have morphological characteristics of neurons, are NCAM or MAP-2 positive, and show a response to one or more of GABA, acetylcholine, ATP, and high sodium concentration, glutamate, glycine, ascorbic acid, dopamine, or norepinephrine. In some embodiments, a subject differentiated NCAM or MAP-2 positive can also exhibit an action potential in a patch-clamp system.

Astrocytes

Astrocytes can also be produced from a subject induced NSC. Astrocytes can be generated by culturing induced NSCs in B27 medium. Astrocytes can be generated by culturing induced NSCs in the presence of neurogenic medium with bFGF and EGF; see e.g., Brustle et al. (1999) *Science* 285: 754-756.

Astrocytes can be identified by expression of astrocyte markers GFAP (glial fibrillary acidic protein; see, e.g., McKeever (1992) *Cell Mol. Biol.* 38:175); S100β; and the like. For GFAP, see, e.g., GenBank Accession Nos. P14136 and AAB22581.

Oligodendrocytes

Oligodendrocytes can be generated from a subject induced NSC. Differentiation of a subject induced NSC into oligodendrocytes can be accomplished by known methods. For example, oligodendrocytes can be generated by co-culturing a subject induced NSC with stromal cells, e.g., Hermann et al. (2004), *J Cell Sci.* 117(Pt 19):4411-22. In another example, oligodendrocytes may be generated by culturing a subject induced NSC in the presence of a fusion protein, in which the Interleukin (IL)-6 receptor, or derivative, is linked to the IL-6 cytokine, or derivative thereof. Oligodendrocytes can also be generated from a subject induced NSC by other methods known in the art, see, e.g. Kang et al., (2007) *Stem Cells* 25, 419-424.

Oligodendrocytes may be identified by expression of oligodendrocyte markers GC (galactocerebroside, also referred to as GalC); MBP (myelin basic protein); CNPase (2',3'-cyclic nucleotide 3'-phosphodiesterase [or -phosphohydrolase]); or the oligodendrocyte markers neuroendocrine-specific protein-4 (NSP4; also known as reticulon-4 or RTN4), RIP (2',3'-cyclic nucleotide 3'-phosphodiesterase; Friedman et al. (1989) *Glia* 2:380; Watanabe et al. (2006) *J. Neurosci. Res.* 84:525), myelin/oligodendrocyte specific protein (MOSP; Mu and Dyer (1994) *Neurochem. Res.* 19:1033), oligodendrocyte lineage transcription factor 2 (Olig2; see, e.g., GenBank Accession No. NP_005797; and Yokoo et al. (2004) *Am. J. Pathol.* 164:1717), oligodendrocyte marker O1 (Sommer and Schachner (1981) *Dev. Biol.* 83:311), NogoA (see, e.g., GenBank Accession Nos. BAE45717 and BAE45714), or oligodendrocyte marker O4 (Sommer and Schachner (1981) *Dev. Biol.* 83:311).

Purification of Differentiated Cells

Optionally, the differentiated cells can be sorted based on phenotypic features to enrich for certain populations. Typically, this will involve contacting each cell with an antibody or ligand that binds to a marker characteristic of neural cells, followed by separation of the specifically recognized cells from other cells in the population. One method is immunopanning, in which specific antibody is coupled to a solid surface. The cells are contacted with the surface, and cells not expressing the marker are washed away. The bound cells are then recovered by more vigorous elution. Variations of this are affinity chromatography and antibody-mediated magnetic cell sorting. In a typical sorting procedure, the cells are contacted with a specific primary antibody, and then captured with a secondary anti-immunoglobulin reagent bound to a magnetic bead. The adherent cells are then recovered by collecting the beads in a magnetic field.

Another method is fluorescence-activated cell sorting, in which cells expressing the marker are labeled with a specific antibody, typically by way of a fluorescently labeled secondary anti-immunoglobulin. The cells are then separated individually according to the amount of bound label using a suitable sorting device. Any of these methods permit recovery of a positively selected population of cells that bear the marker of interest, and a negatively selected population of cells that not bear the marker in sufficient density or accessibility to be positively selected. Negative selection can also be effected by incubating the cells successively with a specific antibody, and a preparation of complement that will lyse cells to which the antibody has bound. Sorting of the differentiated cell population can occur at any time, but it has generally been found that sorting is best effected shortly after initiating the differentiation process.

Compositions Comprising Differentiated Cells

The present disclosure provides a composition comprising a neuron, an astrocyte, or an oligodendrocyte, generated as described above. In some embodiments, a subject neuron, astrocyte, or oligodendrocyte is genetically modified, e.g., the neuron, astrocyte, or oligodendrocyte comprises the same genetic modification as a subject NSC, where the genetic modification comprises an exogenous Sox2 nucleic acid.

In some embodiments, a subject composition comprises a substantially pure population of neurons that have been generated by inducing a subject induced NSC to differentiate into neurons, where the population comprises at least about 75%, at least about 80%, at least about 85%, at least about 90%, at least about 95%, at least about 98%, at least about 99%, or more than 99%, neurons. In some embodiments, a subject composition comprises a substantially pure population of astrocytes that have been generated by inducing a subject induced NSC to differentiate into astrocytes, where the population comprises at least about 75%, at least about 80%, at least about 85%, at least about 90%, at least about 95%, at least about 98%, at least about 99%, or more than 99%, astrocytes. In some embodiments, a subject composition comprises a substantially pure population of oligodendrocytes that have been generated by inducing a subject induced NSC to differentiate into oligodendrocytes, where the population comprises at least about 75%, at least about 80%, at least about 85%, at least about 90%, at least about 95%, at least about 98%, at least about 99%, or more than 99%, oligodendrocytes.

A subject composition can comprise a neuron, an oligodendrocyte, or an astrocyte, and a suitable liquid culture medium. The composition can in some embodiments include a cryopreservative agent.

A subject composition can comprise a neuron, an oligodendrocyte, or an astrocyte; and a matrix component. Suitable matrix components include, e.g., collagen; gelatin; fibrin; fibrinogen; laminin; a glycosaminoglycan; elastin; hyaluronic acid; a proteoglycan; a glycan; poly(lactic acid); poly (vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly (propylene glycol) flanked by two hydrophilic blocks of poly (ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

The cell density in a subject differentiated cell (e.g., neuron, oligodendrocyte, or astrocyte)/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Utility

A subject iNSC, as well as differentiated cells derived from a subject iNSC, is useful in various applications, which are also provided in the present disclosure.

Research Applications

A subject iNSC can be used in a variety of research applications. For example, a subject iNSC can be introduced into a non-human animal model of a neurological disease; and the effect of the iNSC on the course of the neurological disease can be determined. As another example, a subject iNSC can be introduced into a non-human animal model, where the animal model lacks expression of a specific factor; and the effect of the lack of the factor on differentiation of the introduced iNSC can be determined. As another example, a subject iNSC can be introduced into a non-human animal model, where the animal model overexpresses a specific factor; and the effect of overexpression of the factor on differentiation of the introduced NSC can be determined.

Various non-human animal models for testing restoration of nervous system function are described in "CNS Regeneration: Basic Science and Clinical Advances", M. H. Tuszynski & J. H. Kordower, eds., Academic Press, 1999.

Similarly, a neuron, astrocyte, or oligodendrocyte differentiated from a subject iNSC can be tested in a non-human animal model. For example, a subject neuron, astrocyte, or oligodendrocyte can be introduced into a non-human animal model of a neurological disease; and the effect of the introduced neuron, astrocyte, or oligodendrocyte on the course of the disease can be determined.

Screening Methods

A subject iNSC can be used in a screening method. A subject screening method can be used to identify, e.g.: 1) an agent that enhances self-renewal properties of an NSC; 2) an agent that induces differentiation of an NSC into a neuron, an astrocyte, or an oligodendrocyte; 3) an agent that prolongs survival of a cell differentiated from a subject iNSC; and the like.

For example, in some embodiments, the present disclosure provides a method of identifying a candidate agent for inducing differentiation of an NSC into a neuron, an astrocyte, or an oligodendrocyte, where the method generally involves contacting a population of a subject induced NSC in vitro with a test agent; and determining the effect (if any) of the test agent on inducing differentiation of the NSC into a neuron, an astrocyte, or an oligodendrocyte. A test agent that induces at least 50% of the population of NSC to differentiate (e.g., into a neuron, an oligodendrocyte, or an astrocyte) is considered a candidate differentiation agent.

Other screening applications of this disclosure relate to the testing of pharmaceutical compounds for their effect on neural tissue or nerve transmission. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention, such as dopaminergic, serotonergic, cholinergic, sensory, and motor neurons, oligodendrocytes, and astrocytes. For example, in some embodiments, a subject screening method involves contacting a subject NSC (or a neuron, oligodendrocyte, or astrocyte derived therefrom) with a test agent; and determining the effect of the test agent on response of the subject NSC (or a neuron, oligodendrocyte, or astrocyte derived therefrom) to a neurotransmitter or a ligand for a neurotransmitter receptor (e.g., an agonist, or an antagonist).

Assessment of the activity of candidate pharmaceutical compounds generally involves combining subject NSC (or a neuron, oligodendrocyte, or astrocyte derived therefrom) with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. $^3$H-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Effect of cell function can be assessed using any standard assay to observe phenotype or activity of neural cells, such as receptor binding, neurotransmitter synthesis, release or uptake, electrophysiology, and the growing of neuronal processes or myelin sheaths, e.g., in cell culture or in an appropriate model.

As an example, whether a test agent induces differentiation of a subject NSC can be determined using an immunoassay, as described above, to test for induction of a neuron-specific marker, an oligodendrocyte-specific marker, or an astrocyte-specific marker. As another example, whether a test agent alters a response to an agonist or an antagonist can be determined using standard assays for response to the agonist or antagonist (e.g., calcium flux, etc.)

A subject screening method generally includes appropriate controls, e.g., a control sample that lacks the test agent. Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents such as salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

A test agent can be a small molecule. The test molecules may be individual small molecules of choice or in some cases, the small molecule test agents to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al., (1994), J. Med. Chem., 37(9), 1233-1251. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al., (1993), Proc. Natl. Acad. Sci. U.S.A., 90:6909-6913; analogous organic syntheses of small compound libraries, as described in Chen et al., (1994), J. Amer. Chem. Soc., 116:2661-2662; Oligocarbamates, as described in Cho, et al., (1993), Science, 261:1303-1305; peptidyl phosphonates, as described in Campbell et al., (1994), J. Org. Chem., 59: 658-660; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

Therapeutic Applications

A subject iNSC, or a cell differentiated from a subject iNSC, can be used in various therapeutic applications.

For example, a the present disclosure provides a method for performing cell transplantation in a subject in need thereof, the method generally involving: (i) generating an iNSC from a somatic cell of a healthy donor individual, wherein the donor individual is immunocompatible with the subject; and (ii) transplanting one or more cells differentiated from the iNSC into the subject. In some embodiments, the subject and the donor individual are the same individual.

A subject in need thereof includes, e.g., a subject who has been diagnosed with a neurological disorder. Neurological disorders can be due to an inborn error in function, the effect of a disease condition, or the result of an injury.

A subject iNSC, or a differentiated cells (e.g., neurons, astrocytes, oligodendrocytes) obtained by inducing differentiation of a subject iNSC, can also be used for tissue reconstitution or regeneration in a human patient in need thereof.

The cells are administered in a manner that permits them to graft or migrate to the intended tissue site and reconstitute or regenerate the functionally deficient area.

A subject iNSC, or a differentiated cells (e.g., neurons, astrocytes, oligodendrocytes) obtained by inducing differentiation of a subject iNSC, is useful for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells as described herein may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

By way of illustration, neural stem cells are transplanted directly into parenchymal or intrathecal sites of the central nervous system, according to the disease being treated. Grafts are done using single cell suspension or small aggregates at a density of 25,000-500,000 cells per μL (U.S. Pat. No. 5,968, 829). The efficacy of transplants of motor neurons or their precursors can be assessed in a rat model for acutely injured spinal cord as described by McDonald et al. (Nat. Med. 5:1410, 1999). A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

A subject iNSC, or a differentiated cells (e.g., neurons, astrocytes, oligodendrocytes) obtained by inducing differentiation of a subject iNSC, can be supplied in the form of a pharmaceutical composition comprising an isotonic excipient prepared under sufficiently sterile conditions for human administration. For general principles in medicinal formulation, see, e.g., Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

For the treatment of Parkinson's disease, a population of subject iNSCs can be differentiated into dopamine-acting neurons and then transplanted into the striate body of a subject with Parkinson's disease. For the treatment of multiple sclerosis (MS), neural stem cells can be differentiated into oligodendrocytes or progenitors of oligodendrocytes, which are then transferred to a subject suffering from MS.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation of Induced Neural Stem Cells

Materials and Methods
Reagents and Cell Culture

All cells were cultured on tissue culture dishes or plates coated with 0.1% gelatin, 1 μg/ml laminin, or a combination of both substrates. Mouse iNSCs and wild-type NSCs were cultured in NSC basal medium (Millipore) supplemented with 20 ng/ml fibroblast growth factor-2 (FGF-2), 20 ng/ml epidermal growth factor (EGF), and 2 μg/m heparin (NSC-BM+++). NSC basal medium contains Dulbecco's modified Eagle's medium (DMEM)/F12 with 1×B27 CHEM, 2 mM L-glutamine, and 1× penicillin/streptomycin without HEPES. Human iNSCs and NPCs derived from human iPS cells were culture in ReNcell medium (Millipore) supplemented with 20 ng/ml human FGF-2 and 20 ng/ml human EGF (ReNcell++). ReNcell medium consists of DMEM/F12 without HEPES, with L-Glutamine, L-glutamine, human serum albumin, human transferrin, putrescine dihydrochloride, human recombinant insulin, L-thyroxine, tri-iodo-thyronine, progesterone, sodium selenite, heparin, and corticosterone. Mouse and human iNSCs and wild-type NSCs were passaged with Accutase (Chemicon). Mitotically inactive mitomycin C-treated mouse STO feeder cells, MEFs, and HFFs (System Biosciences) were cultured in DMEM with high glucose (Gibco) containing 10% heat-inactivated FBS (Life Technologies), 50 U penicillin, and 50 mg/ml streptomycin. Plat-E packaging cells were cultured in the same medium with puromycin (1 μg/ml) and blasticidin S (10 μg/ml).

Three wild-type mouse NSC lines were used in this study. The SCR029 cell line, which are cortical NSCs derived from E14-18 embryos, were purchased from Chemicon and have been well characterized. Wild-type brain-derived NSCs were generated in our lab from E14.5 cortical primary neuron preps, as reported (Pacey et al., (2006) Nature Protocols, 10.1038/nprot.2006.215). This cell line was characterized in our lab and found to express proper NSC markers such as Sox2 and Nestin and differentiate into all three neural lineages in vitro. Lastly, wild-type NSCs derived from mouse iPS cells (Clone-WT.9 and Clone-411) were generated and characterized in our lab using previously established protocols (Conti et al., (2005) PLoS Biol 3, 1594-1606). Wild-type human NSCs were derived from human iPS cells in our lab using previously established protocols (Conti et al., (2005), supra)

Sox2 Retroviral Reprogramming of Mouse and Human Fibroblasts

Mouse iNSCs were generated from wild-type MEFs (at passages 1-3) by retroviral transduction of the transcription factor Sox2. MEFs were isolated from E18 wild-type mouse embryos. Glass coverslips (Fisher Scientific) were placed in wells of a 24-well culture plate and coated with 0.1% gelatin (Sigma) for 30 minutes at 37° C. Extra gelatin was removed, and mitomycin C-treated mouse STO feeder cells were plated at $1.25 \times 10^5$ cells/well into all wells in DMEM+10% FBS. The next day, wild-type MEFs were plated at $7.5 \times 10^3$ to $4 \times 10^5$ cells/well onto the layer of mitomycin C-treated mouse STO feeder cells. One day later, Sox2 retroviral medium was collected and filtered through a 0.45-μm filter (Millipore), and Polybrene (Sigma) was added (final concentration, 4

μg/ml). The pMX Sox2 retroviral plasmid was a gift; and Sox2 retroviral medium was generated as described (Takahashi et al., (2007) Cell 131, 861-872). Sox2 retroviral medium was mixed with an equal volume of regular DMEM+ 10% fetal bovine serum (FBS). MEFs were then transduced with 500 μl of Sox2 retrovirus for 24 hours and then cultured in NSC-BM+++. The culture medium was changed fully every day. Within 3-4 days after transduction, fibroblast morphology had changed considerably. By six days after transduction, mature networks consisting of thin chains of elongated cells were observed along with small colonies of round, bright cells at the intersections of these networks. These colonies grew and expanded rapidly during days 7-10. The cells were then collected with Accutase (Millipore) and transferred to a fresh six-well plate. At confluency, cells were resuspended in 60-mm Petri dishes with NSC-BM+++ for primary neurosphere formation. After culturing for 5-7 days, spheres were collected by gravity and plated onto gelatin-coated six-well plates for monolayer expansion. At confluency, cells were harvested and resuspended for a second round of neurosphere formation. After three rounds of neurosphere formation, the cells were passaged in monolayer cultures in tissue culture coated plates in NSC-BM+++ every 3-5 days.

For reprogramming of human fetal foreskin fibroblasts (HFFs), human SOX2 (hSOX2) retrovirus was prepared similarly to mouse retrovirus. Fugene transfection was conducted with 8 μg of hSOX2 pMX and 1 μg of pCMV VSVG plasmids. STO feeder cells were plated at $1.25 \times 10^5$ cells/well in 24-well plates. The next day, HFF cells were seeded at $7.5 \times 10^3$ cells/well in DMEM+10% FBS. Twenty-four hours later, the medium was replaced with 250 μl of hSOX2 viral medium and 250 μl of DMEM+10% FBS. The following day, the viral medium was removed and replaced with DMEM+10% FBS. On Day 5, the medium was changed to ReNcell with human recombinant basic FGF2 and EGF, both at 20 ng/ml. Over the next 7 days, reprogrammed cells began generating floating spheres, which were collected and plated in Petri dishes with growth factor medium. These spheres were cultured in ReNcell++ for at least 5 days and transferred to laminin-coated plates for monolayer outgrowth. Reprogrammed cells were subjected to three rounds of neurosphere formation and monolayer passaging, as described for the miNSC cell lines.

Determining miNSC Reprogramming Efficiency

MEFs were seeded on feeder cell layers on either gelatin-coated glass coverslips at $1.25 \times 10^4$ cells/well or poly-L-ornithine/laminin-coated glass coverslips at $7.5 \times 10^3$ cells/well, infected with Sox2 retrovirus for 24 hours as described above, cultured in NSC-BM+++, and fixed with paraformaldehyde at days 8 and 12. The cells were immunostained for Nestin and Sox2, and the number of double-positive colonies was counted (five coverslips per day). The efficiency of colony formation was determined by dividing the average number of double-positive colonies per coverslip by the total starting number of MEFs per well.

NSC Neurosphere Formation

Neurosphere formation was assayed for iNSCs and wild-type NSCs by resuspending $2.0 \times 10^4$ cells in growth medium (NSC-BM+++ or ReNcell++) in a 60-mm bacterial culture dish (non-tissue culture coated). Fresh medium was added each day to the suspension cultures. Six days after suspension, neurospheres were collected and counted with a light microscope.

Bisulfite Sequencing and DNA Methylation Analysis

Genomic DNA was isolated from the following cell lines, miNSC-A21, wild-type SCR029 NSC, and wild-type MEFs, using standard procedures. Bisulfite treatment was conducted for all three samples using the EpiTect Bisulfite Kit (Qiagen). Previously published nested primer sets were used to amplify the promoter regions of the following genes: Sox2, Nestin, and Oct3/4 (Han et al, (2009) Stem Cells, 27, 1088-1097; Imamura et al., (2006) BMC Dev Biol 6, 34; Western et al., (2010) FASEB J 24, 3026-3035). PCR products were subcloned into the PCR 2.1 vector (Invitrogen) and clones that contained inserts were purified using the QlAprep Spin Miniprep kit (Qiagen). Individual clones (10 or more) were sequenced (Elim Biosciences) and only clones with over 90% bisulfite conversion were accepted. Bisulfite conversion of CpG was scored using the online software QUMA or Quantification tool for Methylation Analysis (Kumaki et al., (2008) Nucleic Acids Res 36, W170-W175).

Neuronal, Astrocytic, and Oligodendrocytic Differentiation of iNSCs.

Mouse neurons, astrocytes, and oligodendrocytes were generated by plating $5 \times 10^3$ to $1.5 \times 10^4$ miNSCs onto laminin/gelatin-coated glass coverslips in 24-wells containing NSC-BM+++. After 24 hours, the medium was switched to NSC-BM without growth factors to induce differentiation of NSCs into all three types of neural cells by 2-4 weeks after plating (Hsieh et al., (2004) J Cell Biol 164, 111-122). Robust astrogenesis was induced by adding bone morphogenic protein-4 (BMP4) (50 ng/ml; R&D Biosystems) or 1% FBS to NSC-BM without growth factors (Gross et al., (1996) Neuron 17, 595-606).

Human iNSCs were differentiated in ReNcell medium without growth factors. hiNSCs were seeded at $1.0-1.5 \times 10^3$ cells/well on laminin/gelatin-coated coverslips in ReNcell++. Two days later, the medium was switched to non-growth factor medium, which was changed every 3-4 days. Between 1 and 2 months of differentiation, the cultures were immunostained to identify neurons, astrocytes, and oligodendrocytes. Specific differentiation conditions included neuronal induction with retinoic acid (1 μM) plus forskolin (5 μM) (Hsieh et al., (2004), supra) or WNT5A (100 ng/ml; R&D) (Yu et al., 2006) and astrocyte induction with BMP4 (50 ng/ml) (Gross et al., (1996), supra).

Immunocytochemistry and Image Collection

Cells on glass coverslips were fixed in 4% paraformaldehyde for 15 minutes at room temperature and washed with PBS. Nonspecific antibody binding was blocked, and cells were permeabilized with 10% normal donkey serum (Jackson ImmunoResearch) containing 0.2% Triton X-100 (Sigma) in phosphate-buffered saline (PBS) (PBS-T) for 1 hour at room temperature. Cells were rinsed and then incubated in primary antibody containing 3% normal donkey serum in PBS-T overnight at 4° C. After washing in PBS, cells were incubated in secondary antibody containing 3% normal donkey serum in PBS-T for 1 hour at room temperature. Cells were immunostained with the following primary antibodies: monoclonal mouse anti-Nestin (1:200; Chemicon), monoclonal mouse anti-Nestin human specific (1:200, Chemicon), polyclonal goat anti-Sox2 (1:400; Santa Cruz Biotechnology), monoclonal mouse anti-Pax6 (1:100, DSHB), polyclonal rabbit anti-BLBP (1:300, Chemicon), monoclonal mouse anti βIII tubulin (1:800; Promega), polyclonal rabbit anti-MAP2 (1:250; Chemicon), monoclonal mouse anti-MAP2 (1:100; Chemicon), polyclonal rabbit anti-Tau (1:1000, Sigma), monoclonal mouse anti-vGlut1(1:100; Chemicon), polyclonal rabbit anti-GABA (1:1000, Sigma), polyclonal rabbit anti-Synapsin (1:1000; Chemicon); polyclonal rabbit anti-Olig2 (1:500, Chemicon), polyclonal rabbit anti-glial fibrillary acidic protein (GFAP, 1:400; DakoCytomation), and monoclonal mouse anti-O4 (1:50; Chemicon). Primary antibodies were detected with the following fluorescently tagged secondary antibodies: donkey anti-rabbit, donkey anti-goat, or donkey anti-mouse Alexa488 IgG, Alexa594 IgG, Alexa647 IgG, or Alexa488 IgM (1:1000; Invitrogen). Coverslips with stained cells were mounted on glass slides in VectaShield mounting medium that contained DAPI. Stained cells were examined with a Radiance 2000 laser-scanning confocal system (Bio-Rad) mounted on a Nikon Optiphot-2 microscope. Images were processed with Photoshop CS (Adobe Systems)

RNA Isolation and Real-Time qRT-PCR Analysis

Total RNA was isolated from mouse and human cell lines with the RNeasy Mini Kit (Qiagen) with DNase I digestion (Sigma). Complementary DNA was generated from 1-3 µg of total RNA with the RT$^2$ First Strand Kit (Qiagen). Real-time quantitative polymerase chain reaction (qPCR) was performed with custom mouse and human RT$^2$ Profiler 96-well PCR arrays (SABiosciences) and SYBR Green. See Tables 1 and 2 for PCR Array gene lists. For qPCR of endogenous and exogenous Sox2 expression, previously published primer sets were used (Takahashi and Yamanaka, (2006) Cell 126, 663-676).

TABLE 1

Custom Mouse RT$^2$Profiler PCR Array

| Symbol | GenBank | Description |
|---|---|---|
| Pou5f1 | NM_013633 | POU domain, class 5, transcription factor 1 |
| Nanog | NM_028016 | Nanog homeobox |
| Zfp42 | NM_009556 | Zing finger protein 42 |
| Sox2 | NM_011443 | SRY box containing gene 2 |
| Nes | NM_016701 | Nestin |
| Pax6 | NM_013627 | Paired box gene 6 |
| Sox1 | NM_009233 | SRY-box containing gene 1 |
| Zbtb16 | NM_001033324 | Zinc finger and BTB domain containing 16 |
| Msi1 | NM_008629 | Musashi homolog 1 (*Drosophila*) |
| Gfap | NM_010277 | Glial fibrillary acidic protein |
| Mtap2 | NM_001039934 | Microtubule-associated protein 2 |
| Neurod1 | NM_010894 | Neurogenic differentiation 1 |
| Gapdh | NM_008084 | Glyceraldehyde-3-phosphate dehydrogenase |
| MGDC | SA_00106 | Mouse Genomic DNA Contamination |
| RTC | SA_00104 | Reverse Transcription Control |
| PPC | SA_00103 | Positive PCR Control |

TABLE 2

Custom Human RT$^2$Profiler PCR Array

| Symbol | GenBank | Description |
|---|---|---|
| POU5F1 | NM_002701 | POU class 5 homeobox 1 |
| NANOG | NM_024865 | Nanog homeobox |
| ZFP42 | NM_174900 | Zing finger protein 42 homolog (mouse) |
| SOX2 | NM_003106 | SRY (sex determining region Y)-box 2 |
| NES | NM_006617 | Nestin |
| PAX6 | NM_000280 | Paired box 6 |
| SOX1 | NM_005986 | SRY (sex determining region Y)-box 1 |
| ZBTB16 | NM_006006 | Zinc finger and BTB domain containing 16 |
| MSI1 | NM_002442 | Musashi homolog 1 (*Drosophila*) |
| GFAP | NM_002055 | Glial fibrillary acidic protein |
| MAP2 | NM_002374 | Microtubule-associated protein 2 |
| NEUROD1 | NM_002500 | Neurogenic differentiation 1 |
| GAPDH | NM_002046 | Glyceraldehyde-3-phosphate dehydrogenase |
| HGDC | SA_00105 | Human Genomic DNA Contamination |
| RTC | SA_00104 | Reverse Transcription Control |
| PPC | SA_00103 | Positive PCR Control |

Electrophysiology Studies miNSCs were differentiated for 2-4 weeks on laminin-coated coverslips in NSC-BM without EGF or FGF2 and switched to primary neuron media 24 hours before being transferred to a fixed stage for electrophysiology experiments. Primary neuron medium consists of Neural Basal medium (Gibco), 1×B27 CHEM, 1% Pen/Strep, and 1× Glutamax. Whole-cell patch clamp recordings were obtained from visually identified cells with neuronal-like processes. Coverslips were immersed in a HEPES-buffered saline solution containing (in mM) 115 NaCl, 2 KCl, 10 HEPES, 1.5 $MgCl_2$, 3 CaCl, and 10 glucose. All experiments were performed at room temperature. Resistance of borosilicate glass micropipettes was 2-4 MOhm when filled with the following (in mM): 130 $KMeSO_3$, 10 NaCl, 2 $MgCl_2$, 0.16 $CaCl_2$, 10 HEPES, and 0.5 EGTA. Recordings were obtained using a MultiClamp 700B amplifier (Molecular Devices), filtered at 2 kHz, and digitized at 10 kHz. Whole-cell capacitance and membrane resistance were determined from a transient 5 mV hyperpolarizing step from a holding potential of −70 mV. Data were acquired and analyzed online with custom Igor Pro software.

In Vivo iNSC Studies

For in vivo integration and differentiation studies, green fluorescent protein (GFP)-labeled miNSC-A21 were grown in suspension dishes in NSC-BM plus growth factors for 24 hours to generate small neurospheres. Neurospheres were collected and microinjected into the cortices of P2-3 pups (CD1 genetic background). Pups were anesthetized on ice and placed in a customized head mold. ~$3×10^4$ cells in 50 nl volumes were injected into 4 sites on a single hemisphere between bregma and lambda at a 25 degree angle towards the midline at a depth of 0.26 mm using a Nanoject by Drummond on a Kopf stereotaxic frame. Brains were collected at 1, 2, and 5 days post injection following a saline perfusion, fixed in 4% paraformaldehyde for 24 hours, washed with PBS, soaked in 30% sucrose for 48 hours and sectioned into 50-µm coronal sections with a sliding microtome. Brain sections were immunostained for NeuN (neurons), GFAP (astrocytes), and Olig2 (oligodendrocytes) using methods described previously.

Tumorigenesis studies were conducted as follows. miNSC, wild-type NSC, and iPS cell-derived NSC lines, as well as hiNSC lines were cultured simultaneously and harvested for stereotaxic injection. Cells were resuspended at $1.0×10^3$ cells/µl in PBS and incubated on ice. Mice were anesthetized using standard procedure. Cell injections were targeted to the hippocampus of 3-12-month-old non-obese diabetic/severe combined immunodeficiency (NOD/SCID) mice (Jackson Laboratory) (x: ±1.5 mm, y: 2.1 mm, z: 2.1 mm) Side-by-side-injections into the hippocampus were performed with implanted bilateral cannulas held in place by an adaptor. Cells were delivered to the hippocampal area via an injector that was inserted into the cannula (0.1 µl/min, 1 µl volume per side). After transplantation, the cannula was slowly and carefully removed, and the heads were closed up. Injected mice were euthanized at 4-6 weeks and perfused with saline. Brains were fixed in 4% paraformaldehyde for 48 hours, washed with PBS, incubated in 30% sucrose for 48 hours, and cut with a sliding microtome into 30-µm coronal sections. The slices were then immunostained for neural stem cell, neuronal, and glial markers to determine the presence of tumors.

Statistical Analyses

Values are expressed as mean±SD. Differences between means were assessed by t test or analysis of variance (ANOVA). $P<0.05$ was considered statistically significant.

Results

Generation and Characterization of iNSCs from Mouse Fibroblasts

The protocol for generating iNSCs from mouse embryonic fibroblasts (MEFs) is shown in FIG. 1A. In choosing the reprogramming factors, five key transcription factors—Sox2, Bmi-1, TLX, Hes1, and Oct1, were considered. Sox2, Bmi-1, TLX and Hes1 are key transcription factors that are highly expressed in NSCs and are important in NSC production, maintenance, self-renewal, and proliferation (Graham et al., (2003) Neuron 39, 749-765; Jin et al., (2009) J Biol Chem 284, 8160-8173; Kageyama et al., (2008) Dev Growth Differ 50, S97-S103; Molofsky et al., (2003) Nature 425, 962-967; Shi et al., (2004) Nature 427, 78-83; Suh et al., (2007) Cell Stem Cell 1, 515-528). Oct1 is a POU class 2 transcription factor that is expressed in the developing neural tube, binds to the Nestin enhancer during embryonic development, and directly interacts with Sox2 on the transcriptional level (Jin et al., (2009), supra; Williams et al., (2004) J Biol Chem, 279, 1449-1457). These transcription factors were expressed individually or in different combinations in MEFs by retrovirus-mediated gene transduction. In pilot studies, the morphology of MEFs cultured on gelatin-coated plastic in NSC medium supplemented with growth factors (Epidermal Growth Factor (EGF) and Fibroblast Growth Factor (FGF2)) was unchanged for up to 4 weeks after transduction (FIG. 1A-Step 1). However, when MEFs were cultured on glass coverslips coated with gelatin, their morphology was drastically altered by retroviral Sox2 alone (FIGS. 1A-Step 2, 1B, 1C) or by Sox2 plus additional transcription factors. Since the combination of different transcription factors with Sox2 did not enhance the reprogramming efficiency, and in some cases yielded less encouraging results, studies were focused on using Sox2 alone.

By 2-10 days after transduction with Sox2, transformed cells had formed networks and established colony-like cell clusters at the intersections of these networks (FIG. 1A-Step 2, FIG. 1C). Many of these clusters were positive for Sox2 and Nestin, as shown by immunofluorescence staining (FIG. 1D), suggesting that they expressed Sox2 and began to express the NSC marker Nestin. The efficiency of generating Sox2 and Nestin double-positive colony-like clusters on gelatin-coated coverslips was 0.13% at day 8 and 0.52% at day 12 (Table 3). However, most cells along the networks were negative for Sox2 and Nestin (FIG. 1D). Additionally, the efficiency of generating Sox2 and Nestin double-positive colony-like clusters was enhanced to 0.96% at 8 days post infection by culturing infected cells on Poly-L-Ornithine- and Laminin-coated coverslips (Table 3). This alternate coating condition is known to be more conducive to the growth and passage of NSCs in vitro (Lee et al., (2007) Nature Biotechnol 25, 1468-1475). Furthermore, immunostaining of Sox2-infected cells 14 days post infection in NSC-media with growth factors revealed the lack of MAP2-positive neurons, GFAP-positive astrocytes, and O4-positive oligodendrocytes, indicating that Sox2 transduction does not generate differentiated neural cells directly (Table 4) Importantly, no morphological changes and no Nestin- or Sox2-positive cells were observed in MEFs not transduced with Sox2 (FIG. 1E) or MEFs cultured on gelatin-coated plastic up to 4 weeks after retroviral Sox2 transduction. Furthermore, untransfected MEFs did not stain positive for the differentiated cell markers MAP2, GFAP, and O4 (Table 4). It was concluded that there were no contaminating neural progenitor, neural crest, neuronal or glial cells in our MEF cell populations.

TABLE 4

Neural marker immunostaining of MEFs with or without Sox2 retroviral infection in NSC media with growth factors

| Condition | Days in vitro | Map2 | GFAP | O4 | Nestin | Sox2 |
|---|---|---|---|---|---|---|
| MEFs + Sox2 retrovirus | 14 | − | − | − | + | + |
| MEFs − Sox2 retrovirus | 14-28 | − | − | − | − | − |

Six to ten days after retroviral Sox2 transduction, cell mixtures containing multiple colony-like clusters were collected and re-cultured in gelatin-coated six-well plates without glass coverslips to promote cell proliferation and expansion (FIG. 1A-Step 3). At this stage, the cells represented a mixture with different morphologies and were thought to contain untransformed MEFs, partially reprogrammed cells, and potentially fully reprogrammed NSCs (FIG. 1F). Five days later, Sox2-infected cells were released for primary neurosphere culture in suspension to select for NSC-like cells (FIG. 1A-Step 4). The primary neurospheres were seeded into gelatin-coated six-well plates (FIG. 1A-Step 5), and cells with NSC-like morphology grew gradually from adhered neurospheres. To further enrich and purify potentially reprogrammed NSC-like cells, the neurosphere culture procedures were repeated twice (second and third neurospheres, FIG. 1A-Steps 4 and 5). After the third neurosphere culture, the NSC-like cells were grown in monolayer culture for many generations (FIG. 1A-Step 6 and 1G). During the first few monolayer passages, there was a mixture of NSC-like cells (majority) and cells with various other morphologies (minority). However, by five passages, most cells with varying morphologies were lost, and NSC-like cells with bipolar morphology were predominant. Further passaging as a monolayer in NSC medium with growth factors resulted in a homogenous population of NSC-like cells. The reprogrammed NSC-like cells at passages 8, 11 (FIG. 1H), and 28 (FIG. 1I) had morphologies very similar to those of wild-type mouse NSCs (FIG. 1J). Similar results were obtained from independent reprogramming experiments using the same protocol, demonstrating the repeatability of this reprogramming method.

FIGS. 1A-J. Generation of iNSCs from Mouse Fibroblasts.

(A) Schematic describing the retroviral Sox2 reprogramming protocol. MEFs were infected with Sox2 retrovirus and cultured in NSC medium with growth factors on gelatin-coated glass coverslips for 6-10 days and subjected to three rounds of neurosphere suspension to isolate and enrich reprogrammed NSC-like cells. NSC-like cells were enriched by further passaging in monolayer culture in NSC medium with growth factors. (B) Phase-contrast image of MEFs after overnight treatment with Sox2 retrovirus in fibroblast medium. (C) Sox2-infected cells in NSC medium with growth factors generate networks and colonies on gelatin-coated glass cov-

TABLE 3

Efficiency of generating Nestin+/Sox2+ colonies from MEFs using retroviral Sox2 on Different Substrate-Coated Glass Coverslips.

| Substrate | Day | Coverslips Counted | Average Number of Nestin+/Sox2+ Colonies | Starting MEF Population per Well | Efficiency of Colony Formation |
|---|---|---|---|---|---|
| Gelatin | 8 | 5 | 16 | $1.25 \times 10^4$ | 0.13% |
| Gelatin | 12 | 5 | 65.2 | $1.25 \times 10^4$ | 0.52% |
| Poly-L-Ornithine/Laminin | 8 | 5 | 72.2 | $7.5 \times 10^3$ | 0.96% | erslips by 8 days after infection. (D) Sox2-transformed colonies are positive for the NSC markers Nestin and Sox2. (E) Fibroblasts cultured in NSC medium with growth factors but without Sox2 retroviral transduction do not generate colonies or networks. (F) Sox2-transduced cells after 11 days have drastically different morphology from their fibroblast counterparts. (G) After three rounds of neurosphere generation, reprogrammed cells take on the characteristic bipolar NSC morphology. (H) After multiple passages as a monolayer, NSC-like cells are a morphologically homogenous population. (I) Morphology of NSC-like cells stays the same over prolonged passaging, and reprogrammed cells can proliferate over 28 passages. (J) The morphology of NSC-like cells is similar to that of wild-type cortical-derived NSCs such as the commercial cell line SCR029 (Millipore). Scale bars=50 µm in B and E-J; scale bars=100 µm in C and D.

The reprogrammed mouse NSC-like cells expressed NSC markers, including Sox2 and Nestin, similarly to the wild-type cortical mouse NSC line, SCR029 (Chemicon) (FIGS. 2A-2D) as well as Pax6, and BLBP, as shown by immunostaining. Quantitative real-time RT-PCR (qRT-PCR) confirmed that NSC-like cells express the NSC marker genes Sox2 and Nestin, and additionally expressed Sox1 and Zbtb16 (FIG. 1E); however, even at low passages, they did not express pluripotency-related genes, such as Oct4, Nanog, and Zfp42 (FIG. 1F), nor did they express Oct4 or Nanog during the early reprogramming stages. In contrast, MEFs cultured in fibroblast or NSC medium for up to 4 weeks did not show significant expression of Sox2, Nestin, Pax6, Zbtb16, or Msi1, suggesting that simply culturing MEFs in NSC medium does not automatically turn on NSC-related gene expression. It was next determined whether reprogrammed NSC-like cells had silenced retroviral exogenous Sox2 expression and turned on endogenous Sox2 expression similarly to the wild-type NSCs. qRT-PCR was conducted on reprogrammed cells at early passage (P7) and later passage (P16) and compared the exogenous and endogenous Sox2 expression to wild-type NSCs. Interestingly, endogenous Sox2-specific qRT-PCR detected low level of endogenous Sox2 expression in reprogrammed NSC-like cells at passage 7 and significant levels of exogenous Sox2 expression compared to wild-type NSCs. In contrast, reprogrammed NSC-like cells at later passage had more comparable levels of endogenous Sox2 expression to wild-type NSCs at passage 16, suggesting that the endogenous Sox2 gene was gradually turned on in Sox2-reprogrammed NSC-like cells over continuous passaging. Exogenous Sox2-specific qRT-PCR did not detect a significant signal in either reprogrammed NSC-like cells at passage 16 or in wild-type NSCs, consistent with silencing of the retroviral Sox2 transgene in reprogrammed NSC-like cells during continuous passaging. Thus, the reprogrammed NSC-like cells have true endogenous expression of NSC genes and do not require the expression of exogenous Sox2 to maintain their NSC identity at later passages.

Methylation patterns of NSC (Sox2 and Nestin) and ESC (Oct3/4) gene promoters were next analyzed to determine whether miNSCs had properly activated NSC genes, as indicated by hypomethylated CpG, and kept pluripotency genes silenced, as indicated by hypermethylated CpG. miNSCs at passage 12 were compared to wild-type NSCs at passage 17 and MEFs at passage 2 (Han et al., (2009) Stem Cells, 27, 1088-1097; Imamura et al., (2006) BMC Dev Biol 6, 34; Western et al., (2010), supra). Methylation analysis of bisulfite-treated DNA from miNSCs, wild-type NSCs, and MEFs revealed that the Oct3/4 promoter was hypermethylated, indicating the transcriptional silencing of that gene. In contrast, both the Sox2 and Nestin promoters were hypomethylated in miNSCs similarly to wild-type NSCs, indicating that these genes are transcriptionally activated. Thus, miNSCs appropriately activated the transcription of NSC-related genes and keep pluripotency genes, such as Oct3/4, silenced.

Figure 2:
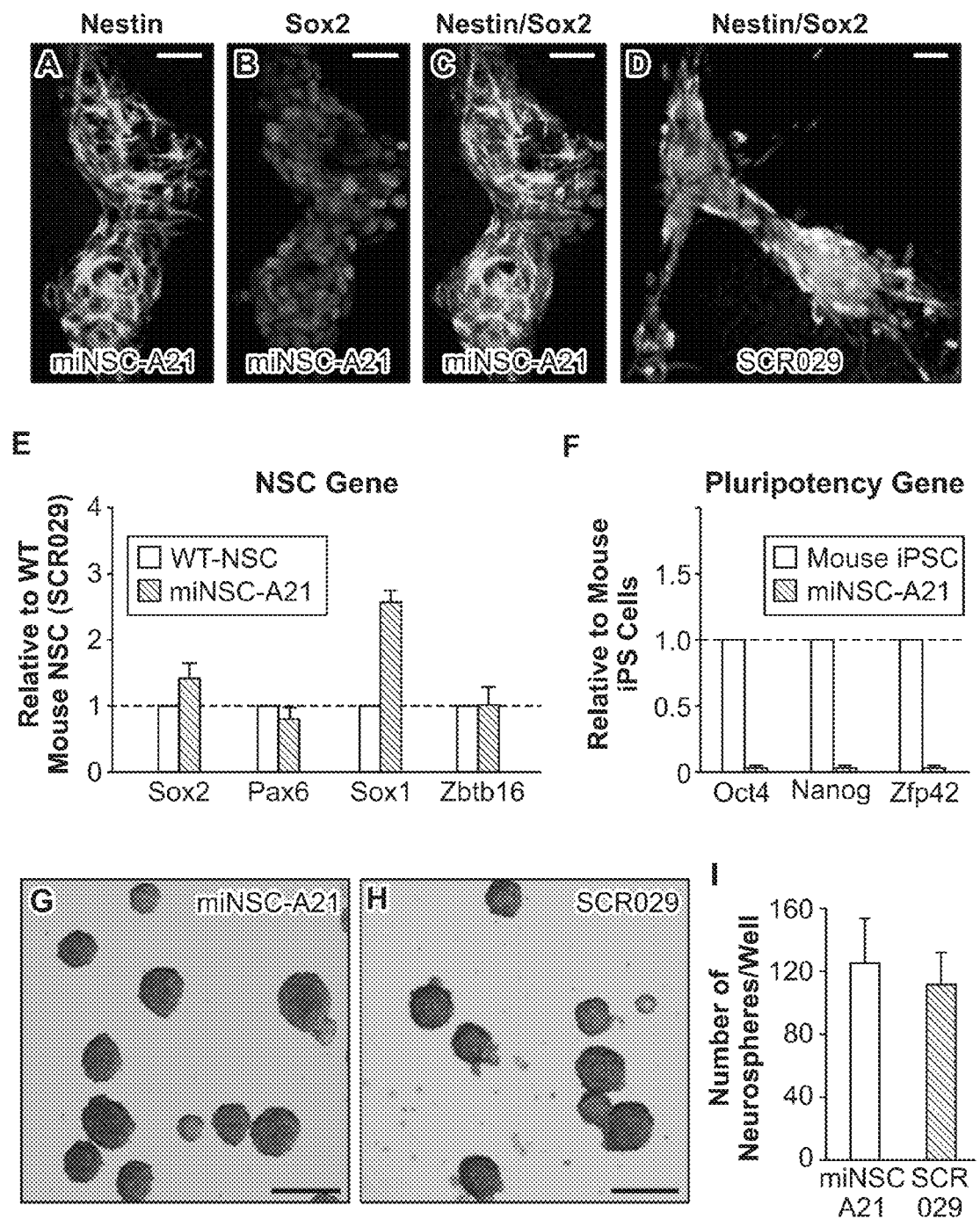
FIGS. 2A-I depict characterization of miNSCs.

Microarray studies demonstrated that the global gene expression pattern of the reprogrammed mouse NSC-like cells was similar to that of wild-type mouse NSCs but different from that of MEFs. Furthermore, like wild-type mouse NSCs, the reprogrammed mouse NSC-like cells formed neurospheres in suspension cultures and do so with similar efficiency (FIGS. 2G-2I). Taken together, these data strongly suggest that a single factor can reprogram MEFs into self-renewing NSCs that appear similar to wild-type NSCs at the transcriptional level and in forming neurospheres. These cells are referred to as mouse induced NSCs (miNSCs).

FIGS. 2A-I. Characterization of miNSCs.

(A-D) For the miNSC-A21 cell line, expression of Nestin and Sox2 is similar to that of brain-derived wild-type NSCs as revealed by immunostaining. (E) qRT-PCR reveals that miNSC-A21 express typical NSC markers. Error bars denote standard deviation of triplicate reactions. (F) qRT-PCR indicates that miNSC-A21 do not express pluripotency related genes. Error bars denote standard deviation of triplicate reactions. (G-I) In suspension culture, miNSC-A21 generates neurospheres similar to wild-type NSCs and with similar efficiency (n=3). Scale bars=50 µm in A-D; scale bars=100 µm in G and H.

Multipotency of miNSCs in Culture

Figure 3:
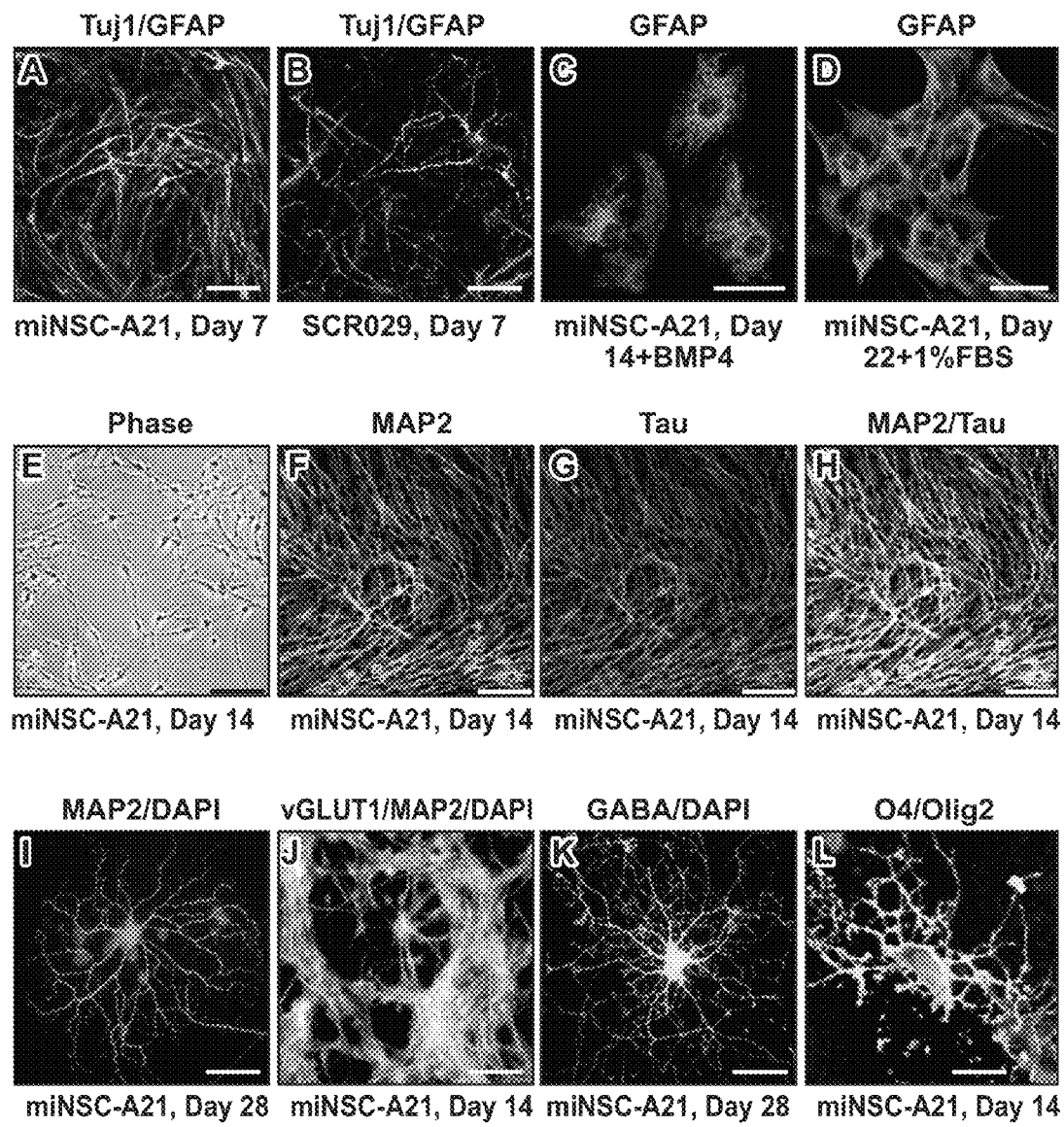
FIGS. 3A-L depict multipotency of miNSCs.
Figure 4:
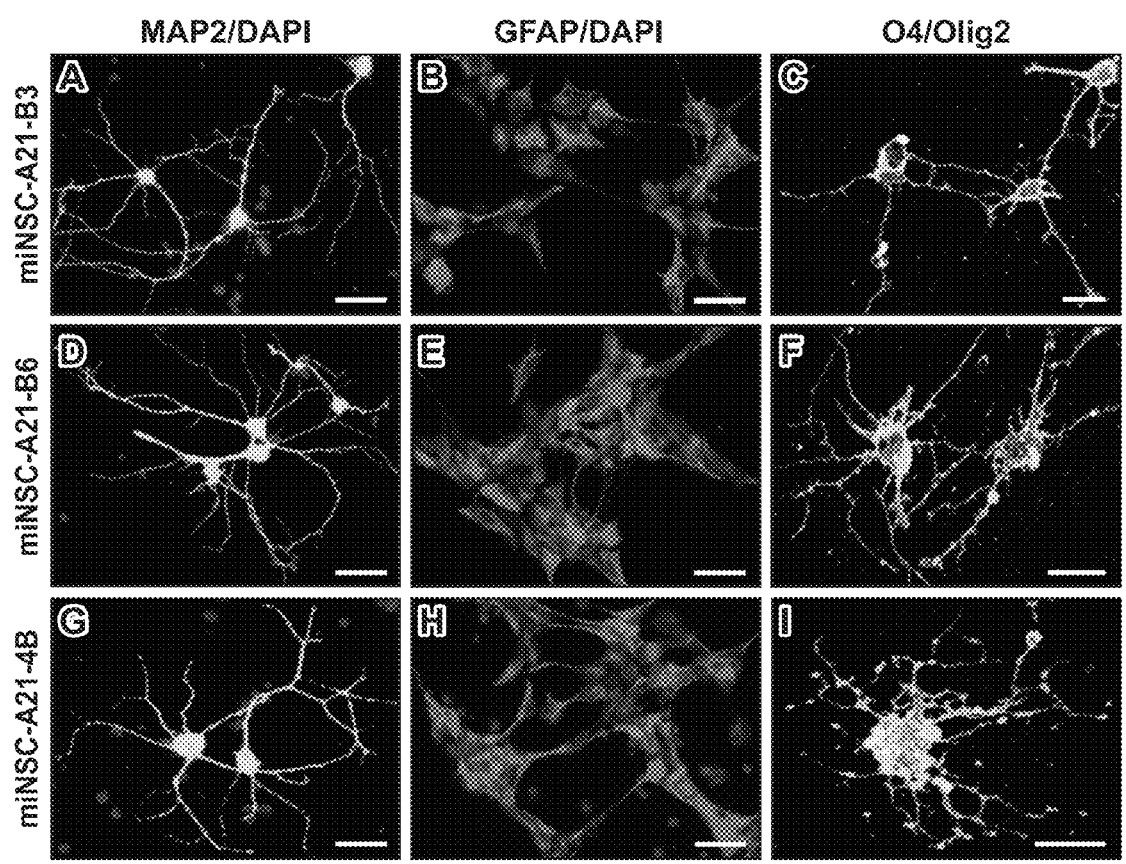
FIGS. 4A-I depict multipotency of cloned miNSC lines.

To assess the neural developmental potential (multipotency) of miNSCs, the ability of miNSCs to differentiate into the three major neural cell types (neurons, astrocytes, and oligodendrocytes) in vitro was tested. Under neuronal differentiation conditions involving removal of growth factors from the NSC medium, miNSCs differentiated into immature neurons (Tuj1-positive) at 1 week in culture similarly to wild-type NSCs (FIGS. 3A-3B) and mature neurons (MAP2- and Tau-positive) at 2 weeks (FIGS. 3E-3H). At 4 weeks, iNSCs developed into MAP2-positive neurons with extensive and complex neurites similar to those of mouse primary neurons in culture (FIG. 3I). At 14-28 days, miNSCs differentiated into vGluT1-positive excitatory neurons (FIG. 3J) and GABA-positive inhibitory neurons (FIG. 3K). Importantly, MAP2-positive mature neurons could be generated from miNSCs at passages P11-P28. Thus, miNSCs have stable neurogenesis capability and their neural fates are not restricted at later passage.

Immunostaining revealed GFAP-positive astrocytes for both miNSCs and wild-type NSCs at 7 days in vitro after the removal of growth factor from the culturing medium (FIGS. 3A-3B). Additionally, a robust population of GFAP-positive astrocytes were derived from miNSCs cultured for 24-22 days under various differentiation conditions, including culturing cells with 50 ng/ml BMP4 or 1% fetal bovine serum (FBS) (FIGS. 3C, 3D). miNSCs also generated astrocytes at early and late passages Importantly, the ability of miNSCs to generate neurons and astrocytes was confirmed in different batches of miNSCs. Furthermore, under oligodendrocyte differentiation conditions involving the removal of growth factors from NSC medium and culturing on gelatin-coated glass coverslips for 2 weeks, miNSCs also developed into oligodendrocytes, as indicated by staining positive for the markers O4 and Olig2 (FIG. 3L). These findings suggest that miNSCs are multipotent, being able to differentiate into all three neural cell populations-neurons, astrocytes, and oligodendrocytes.

FIGS. 3A-L. Multipotency of miNSCs.

(A and B) Like wild-type NSCs, miNSC-A21 can differentiate into Tuj1$^+$ neurons and GFAP$^+$ astrocytes by 7 days in culture after growth factor withdrawal. (C and D) miNSC-A21 can robustly generate GFAP$^+$ astrocytes by 14 days in vitro in the presence of BMP4 or FBS. (E) miNSC-A21 can generate mature looking neurons and neuronal networks by 14 days in culture without growth factors. (F-H) Neurons derived from miNSC-A21 stain positive for the mature neuronal markers MAP2 and Tau. (I) miNSC-A21 can differentiate into mature arborized neurons by 28 days in vitro. (J and K) miNSC-A21 can differentiate into subtypes of neurons, including excitatory vGlut1$^+$ neurons (J) and inhibitory GABA$^+$ neurons (K). (L) miNSC-A21 can generate O4$^+$ and Olig2$^+$ oligodendrocytes by 14 days in culture. Scale bars=50 µm in A, B, E, and J; scale bars=25 µm in C and D; scale bars=75 µm in F-H; scale bars=10 µm in I, K, and L.

To further confirm the multipotency of miNSCs, miNSC-A21 was subcloned at passage 13 when stable NSC gene expression and neuronal differentiation was observed; the multipotency of each clone was then tested. All five clones tested could differentiate into MAP2-positive neurons, GFAP-positive astrocytes, and O4/Olig2 double-positive oligodendrocytes. Representative data from three clones are shown in FIGS. 4A-4I. Thus, miNSCs are a population of truly multipotent NSCs and are not a heterogeneous population of different neural progenitor cells.

FIGS. 4A-I. Multipotency of Cloned miNSC Lines.

(A-I) After 14 days in culture, subcloned lines B3 (A-C), B6 (D-F), and 4B (G-I) of miNSC-A21 can differentiate into MAP2$^+$ mature neurons (A, D, G), GFAP$^+$ astrocytes (B, E, H), and O4$^+$/Olig2$^+$ oligodendrocytes (C, F, I). Scale bars=10 µm in all panels.

The efficiency of neuronal and glial differentiation in vitro for two miNSC clones (A21-B8 and A21-C1) was determined. Under a typical neuronal differentiation condition involving the removal of FGF2 and EGF growth factors from NSC media and differentiation on laminin/gelatin-coated coverslips, the percentages of neurons and astrocytes were determined by counting the numbers of MAP2-positive and GFAP-positive cells, respectively, which were normalized to the total numbers of DAPI-positive nuclei. A similar yield in neurons between the two miNSC-A21 clones (Clone B8: 67±5%; Clone C1: 59±6%), and wild-type brain-derived NSCs (76±6%), was found. However, a higher percentage in astrocytes generated from miNSC-A21 (Clone B8: 25±2%; Clone C1: 18±2%) was found, as compared to wild-type brain-derived NSCs (6±4%). Under this typical neuronal differentiation condition, very few oligodendrocytes were generated.

Functional Neurons Derived from miNSCs

Figure 5:
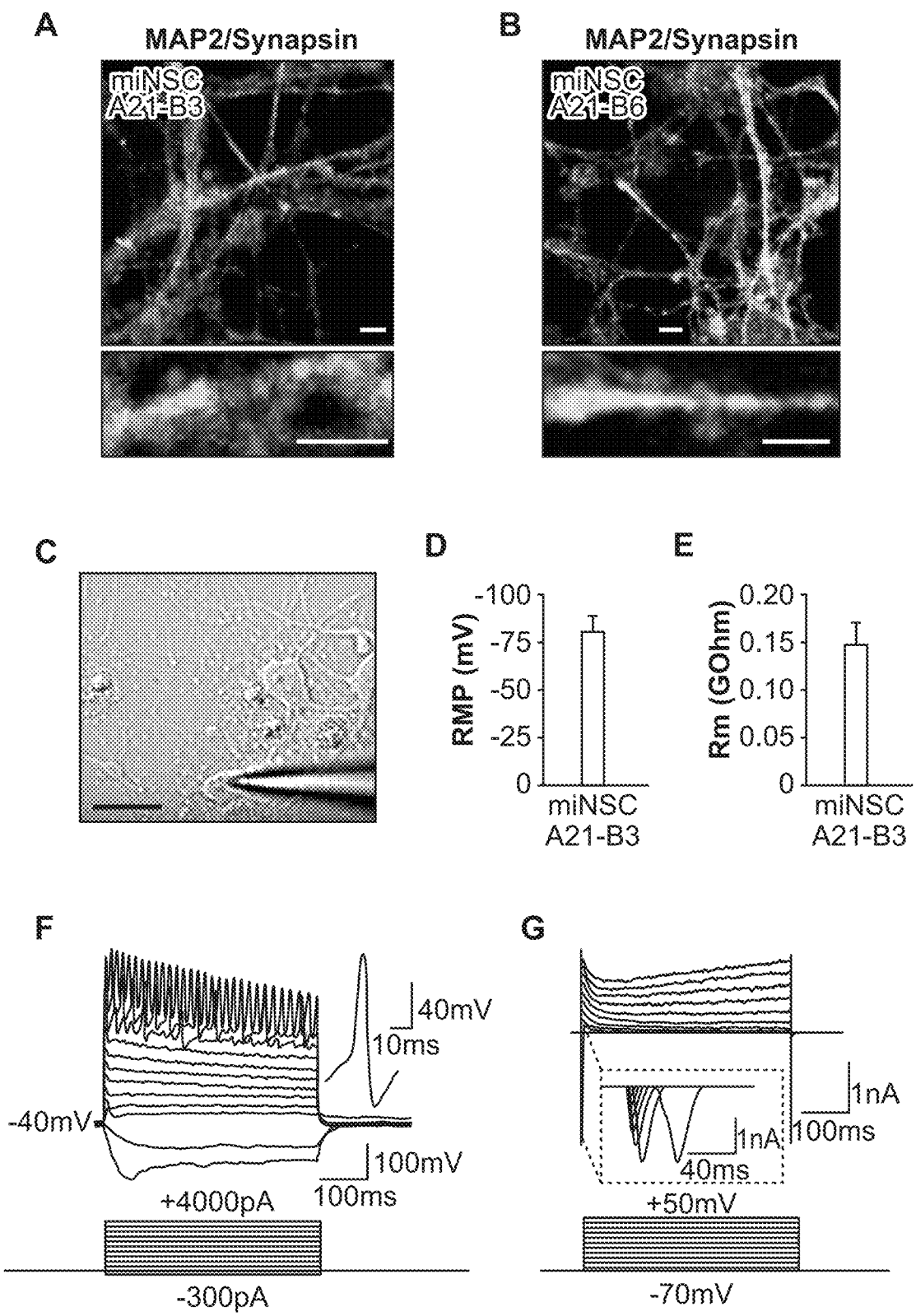
FIGS. 5A-G depict generation of functional neurons from miNSCs.

Mature looking neurons were generated with a protocol that mimics conditions conducive to primary neuron culture. The miNSC-derived neurons developed with this protocol expressed Synapsin, a synaptic marker that is concentrated at the nerve terminals of mature neurons, indicating that miNSC-derived neurons seem to form synaptic connections in vitro (FIGS. 5A and 5B). To test the functionality of miNSC-derived neurons, their electrophysiological properties were characterized by whole-cell patch-clamp recordings (FIG. 5C). At 3 weeks in culture, the neurons had hyperpolarized resting membrane potentials (−40 to −80 mV) (FIG. 5D), and membrane resistance properties (FIG. 5E). Action potentials could be elicited by depolarizing the membrane in current-clamp mode (FIG. 5F). Furthermore, in voltage-clamp mode, both fast inactivating inward and outward currents, which correspond to opening of voltage-dependent Na$^+$ and K$^+$ channels, respectively, were recorded from miNSC-derived neurons (FIG. 5G). Thus, miNSC-derived neurons appear to exhibit the functional membrane properties and activities of normal neurons.

FIGS. 5A-G. Functional Neurons Derived from miNSCs.

(A and B) Neurons derived from subclones miNSC-A21-B3 or miNSC-A21-B6 at 14 days in culture express MAP2 (green) and Synapsin (red), a presynaptic marker of mature neurons. (C) A patched neuron derived from miNSC-A21-B3 at 17 days in culture. (D and E) Whole-cell capacitance and membrane resistance of neurons derived from miNSC-A21 were determined from a transient 5-mV hyperpolarizing step from a holding potential of −70 mV. (F) Current-clamp recordings of neurons derived from miNSC-A21 at −40 mV reveal action potentials with stepwise current injection. (G) Voltage-clamp recordings of neurons derived from miNSC-A21 reveal both fast inactivating inward and outward currents indicating functional voltage-dependent Na$^+$ and K$^+$ channels. Scale bars=2 µm in A and B; scale bar=10 µm in C.

miNSCs can Survive, Integrate, and Differentiate In Vivo

Figure 6:
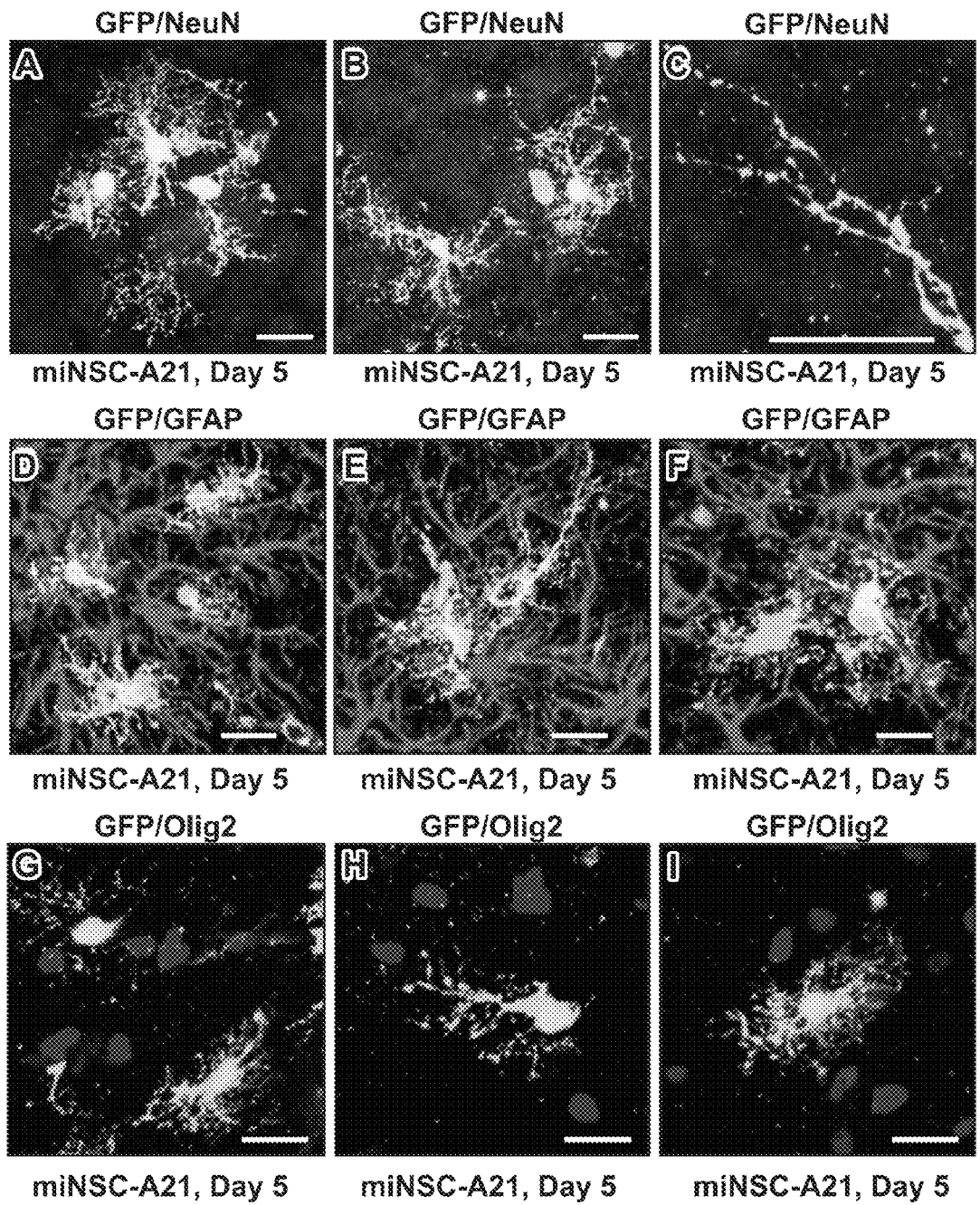
FIGS. 6A-I depict multipotency of miNSCs in vivo.

It was determined whether miNSCs could survive and integrate into the mouse brain. GFP-labeled miNSCs, which were growing 24 hours in suspension cultures in order to generate small neurospheres, were transplanted. It was found that transplanting miNSCs as neurospheres rather than single cells from monolayer cultures resulted in better survival and integration in neonatal brains. miNSCs were micro-injected into the cortex of P2-3 wild-type pups and survival and integration was assessed at 1, 2, and 5 days post transplantation. Immunostaining revealed that miNSCs can differentiate into NeuN-positive neurons with mature-looking dendritic spines (FIGS. 6A-6C), GFAP-positive astrocytes (FIGS. 6D-6F), and Olig2-positive oligodendrocytes, (FIGS. 6G-6I) between 1 and 5 days post transplantation. Thus, miNSCs are capable of differentiating into neurons, astrocytes, and oligodendrocytes both in vitro and in vivo.

FIGS. 6A-I. Multipotency of miNSCs In Vivo.

GFP-labeled miNSC-A21 were grown in suspension cultures for one day to generate small neurospheres and then microinjected into the cortex of P2-3 wild-type pups. Five days after transplantation, mouse brains were collected, fixed, and sectioned. (A-C) Immunostainings reveal that miNSC-A21 can differentiate into NeuN-positive neurons (A and B) with mature looking dendritic spines (C) in vivo. (D-F) miNSC-A21 can also differentiate into GFAP-positive astrocytes in vivo. (G-I) miNSC-A21 can also differentiate into Olig2-positive oligodendrocytes in vivo. Scale bars=10 µm in all panels.

Transplantation of miNSCs into Mouse Brains does not Generate Teratomas

Transplantation of iPS cell-derived neurospheres into mouse brains often results in teratoma formation, while transplantation of multipotent, lineage-restricted brain-derived NSCs does not (Yamanaka, (2009) Cell 137, 13-17). The rate of teratoma formation among miNSCs, mouse iPS cell-derived NSCs, and brain-derived wild-type NSCs was compared. Transplantation of miNSCs or control brain-derived wild-type NSCs into mouse brains did not generate teratomas; however, teratomas formed in over 60% of mice transplanted with mouse iPS cell-derived NSCs. The observation that miNSCs did not form teratomas in vivo in 28 separate hippocampal injections involving three different miNSC-A21 subclones suggests that miNSCs have little or no tumorigenic potential.

Example 2

Generation of Induced Neural Stem Cells from Human Somatic Cells

Induced NSCs can be generated from human somatic cells in a manner similar to that described in Example 1. Human somatic cells (e.g., human dermal fibroblasts, human foreskin fibroblasts, human keratinocytes, human diploid fibroblasts, etc.) are transfected with a retroviral vector that includes a human Sox2 cDNA, e.g., the pMX2-hSox2 plasmid (addgene.org; Retrovirus-mediated gene transfer and expression cloning: powerful tools in functional genomics. Exp Hematol. 2003 November; 31(11):1007-14. Kitamura T, Koshino Y, Shibata F, Oki T, Nakajima H, Nosaka T, Kumagai H.). This Sox2 cDNA lacks the first ATG. As result, the encoded Sox2 protein lacks the first three amino acids; the encoded Sox2 protein is biologically active in reprogramming the somatic cells. Transfection is carried out using Fugene transfection of pMX2-hSox2 together with the vesicular stomatitis virus envelope G protein (VSV-G) expressing packaging plasmid pVSV-G (Yee et al. (1994) *Proc. Natl. Acad. Sci. USA* 91:9563).

The transfected human somatic cells are cultured on gelatin-coated glass coverslips, as described in Example 1, in human neural stem cell medium (Millipore) supplemented with human EGF, human bFGF, and human heparin.

Example 3

Generation of Induced Neural Stem Cells from Human Fibroblasts

The following is a protocol that was used to generate iNSCs from human fibroblasts.
DAY 1:
Plate retroviral packaging cells:
Plate Plat-E cells at $8 \times 10^6$ cells per 10-cm dish (10 mL MEF media). For Plat-E cells, see, e.g., Morita et al. (2000) *Gene Therapy* 7:1063.
DAY 2 and 3:
Plate Human Fibroblasts:
Seed STO cells expressing LIF onto gelatin-coated glass cover slips in a 24-well plate ($1.5 \times 10^6$ cells per 24-well plate). (STO cells: ATCC CRL-1503)
Next day, add human fibroblasts in MEF media into each well with STO cells (7,500-15,000 cells per well).
Transfect Plat-E retroviral packaging cells (based on 10-cm dish):
In a sterile 1.5 ml tube, dilute 27 μl of Fugene (transfection reagent) into 873 μl of Opti-MEM® I Medium without serum. Avoid touching Fugene to side of tube. Mix gently or vortex for 1 second. Incubate for 5 min at room temperature.
Add 8 μg of pMX retroviral vector encoding human SOX2 (hSOX2) together with 1 μg of pCMVVSV-G vector (Addgene Plasmid Repository #8454) to Fugene solution. Mix gently or vortex 1 second. Incubate for 15-45 min at room temperature.
Replace Plat-E cells with 10 mL fresh MEF media.
Add Fugene/DNA complex to 10-cm dish of cells. Mix gently by rocking the plate back and forth. Incubate the cells overnight at 37° C. Change with the fresh medium next day and collect hSox2 virus-containing medium the day after.
DAY 4:
Retroviral Infection of Human Fibroblasts:
Collect retroviral supernatant from each Plat-E flask, filter sterile with 0.45 μm filter, add polybrene (4 μg/m), and add to the human fibroblasts seeded above (250-500 μl of viral medium.
DAY 5 and thereafter:
Keep culturing the infected cells in MEF media (DMEF+ 10% FBS) for 3-5 days.
At day 3-5, change the medium to NSC medium.
At day 7-14, the hSox2-infected cells form networks, which can be collected for further neurosphere and monolayer cultures to generate stable human induced neural stem cells (hiNSCs).

Using this protocol, Nestin-positive cells were obtained by day 14 after infection of human fibroblasts with hSox2 retrovirus. The cells were stable for at least 2 passages.

Example 4

Generation of Induced Neural Stem Cells from Human Fibroblasts

Figure 7:
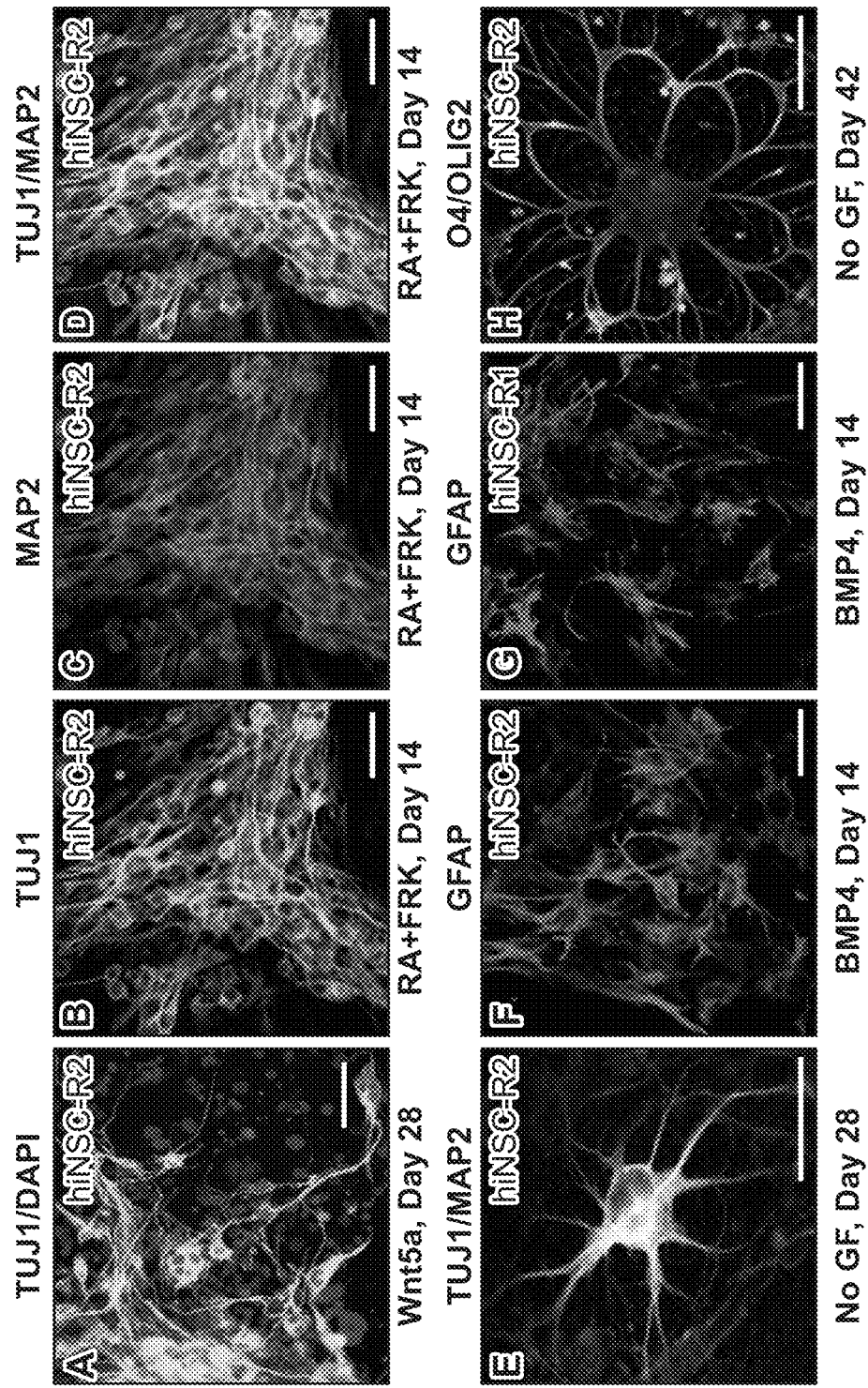
FIGS. 7A-H depict multipotency of hiNSCs.

Human iNSCs (hiNSCs) were generated from human fetal foreskin fibroblasts (HFFs) as described in Example 1. Human iNSCs (hiNSCs) were generated from human fetal foreskin fibroblasts (HFFs) using a protocol similar to that for generating miNSCs (FIG. 1), in which mouse Sox2 was replaced with human SOX2 and reprogrammed cells were cultured in human NSC (hNSC) culture medium supplemented with human EGF and FGF2.
Generation and Characterization of iNSCs from Human Fetal Fibroblasts During reprogramming, the morphological changes in these cells were similar to those in mouse fibroblasts (FIG. 1) Immunostaining revealed that within 5 days after SOX2 retroviral transduction, hiNSC colonies were positive for SOX2 and NESTIN, as shown by immunostaining. After three or four rounds of neurosphere culture, hiNSCs had a morphology similar to that of wild-type human NSCs and could be passaged over 20 generations in culture, like NSCs derived from mouse iPS cells. hiNSCs did not express pluripotency-related genes as determined by qRT-PCR and had neurosphere-forming ability similar to that of NSCs derived from mouse iPS cells.
Multipotency of hiNSCs in Culture To assess the multipotency of hiNSCs, the ability of hiNSCs to differentiate into neurons, astrocytes, and oligodendrocytes in culture was tested. At 2-4 weeks in culture under conditions that favor neuronal differentiation (hNSC medium without growth factors in the presence of WNT5A (100 ng/ml) or retinoic acid (1 μM) plus forskolin (5 μM)), hiNSCs differentiated into immature neurons (TUJ1-positive) and mature neurons (MAP2-positive) (FIGS. 7A-7D). At 4 weeks, hiNSCs developed into MAP2-positive neurons with extensive and complex neurites (FIG. 7E) Importantly, MAP2-positive mature neurons could be generated from hiNSCs at various passages from P8 to P22, suggesting stable neurogenic capacity of hiNSCs. Anti-GFAP immunostaining revealed GFAP-positive astrocytes derived from two separate hiNSC lines cultured for 14 days in the presence of 50 ng/ml BMP4 (FIGS. 7F and 7G). Furthermore, under an oligodendrocyte differentiation condition, hiNSCs also developed into oligodendrocytes, as indicated by positive staining for O4 and OLIG2 (FIG. 7H). It was also confirmed that hiNSCs did not generate teratomas upon transplantation into mouse brains. These data suggest that hiNSCs are multipotent, being able to differentiate into all three neural cell populations-neurons, astrocytes, and oligodendrocytes, and may not harbor any tumorigenic potential in vivo.

FIGS. 7A-J. Multipotency of hiNSCs.

(A) hiNSCs can differentiate into TUJ1$^+$ immature neurons in the presence of the signaling protein WNT5A by 28 days in culture. (B) The addition of retinoic acid (RA) and forskolin (FRK) to neuronal differentiation conditions pushed hiNSCs to differentiate into TUJ1$^+$ neurons by 14 days in vitro. (C and D) hiNSCs can generate TUJ1$^±$/MAP2$^+$ neurons by 14 days in the presence of RA and FRK. (E) hiNSC can generate mature looking neurons that are MAP2$^+$ by 28 days in vitro in hNSC medium without growth factors. (F) hiNSCs can also generate GFAP-positive astrocytes in the presence of BMP4 by 14 days. (G) A separate hiNSC line can also robustly generate GFAP-positive astrocytes at 14 days in vitro. (H) hiNSCs can generate O4/OLIG2 double-positive oligodendrocytes by 40 days in culture in hNSC medium lacking growth factors. Scale bars=20 μm in A-D; scale bars=10 μm in E-H.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated multipotent induced neural stem cell (iNSC) that is genetically modified with a nucleic acid comprising a nucleotide sequence encoding an exogenous Sox2 polypeptide, wherein the multipotent iNSC is not genetically modified with a nucleic acid comprising a nucleotide sequence encoding exogenous Oct-3/4, exogenous c-myc, exogenous Klf4, exogenous Nanog, or exogenous Lin28.

2. The multipotent iNSC of claim 1, wherein the multipotent iNSC is derived from a human somatic cell.

3. A composition comprising the multipotent induced neural stem cell (iNSC) of claim 1.

4. The composition of claim 3, wherein the composition comprises a liquid culture medium.

5. The composition of claim 3, wherein the composition comprises a cryopreservative agent.

6. The composition of claim 3, wherein the composition comprises a matrix component.

7. The multipotent iNSC of claim 1, wherein the multipotent iNSC is a human cell.

8. The multipotent iNSC of claim 1, wherein the multipotent iNSC is a rodent cell.

9. The multipotent iNSC of claim 1, wherein the Sox2 polypeptide comprises an amino acid sequence having at least about 80% amino acid identity to the amino acid sequence set forth in SEQ ID NO:1.

10. The multipotent iNSC of claim 1, wherein the multipotent iNSC is capable of differentiating into a neuron, an astrocyte, or an oligodendrocyte.

* * * * *